United States Patent [19]
Bosmans et al.

[11] Patent Number: 6,096,761
[45] Date of Patent: Aug. 1, 2000

[54] ESTERS OF 3-HYDROXY-PIPERIDINEMETHANOL DERIVATIVES

[75] Inventors: Jean-Paul René Marie Bosmans, Rijkevorsel; John Christopher Love, Deurne; Michel Anna Jozef Decleyn, Merksplas; Henri Elisabeth Frans D'Haen, Vosselaar, all of Belgium

[73] Assignee: Janssen Pharmaceutica N.V., Beerse, Belgium

[21] Appl. No.: 09/117,980

[22] PCT Filed: Feb. 11, 1997

[86] PCT No.: PCT/US97/01681
§ 371 Date: Aug. 11, 1998
§ 102(e) Date: Aug. 11, 1998

[87] PCT Pub. No.: WO97/30031
PCT Pub. Date: Aug. 21, 1997

[30] Foreign Application Priority Data

Feb. 15, 1996 [BE] Belgium .............................. 96200379

[51] Int. Cl.[7] .......................... A01N 43/40; A01N 43/58; C07D 237/30; C07D 401/00; C07D 211/68
[52] U.S. Cl. .......................... 514/317; 514/248; 514/252; 514/256; 514/258; 514/259; 514/315; 514/320; 514/321; 514/322; 514/326; 514/318; 514/317; 544/237; 544/238; 544/278; 544/284; 544/287; 544/335; 544/336; 544/410; 546/194; 546/197; 546/198; 546/199; 546/207; 546/208; 546/210; 546/214; 546/221
[58] Field of Search .................................... 546/221, 197, 546/199, 198, 210, 208, 214, 207, 194; 544/238, 237, 278, 284, 287, 336, 410, 335; 514/315, 321, 320, 322, 326, 318, 252, 248, 258, 259, 256, 317

[56] References Cited

U.S. PATENT DOCUMENTS 5,616,583 4/1997 Van Daele et al. .................. 514/235.5
5,739,134 4/1998 Van Daele et al. ..................... 514/249

FOREIGN PATENT DOCUMENTS

| 0 299 566 | 1/1989 | European Pat. Off. . |
| 0 309 043 | 3/1989 | European Pat. Off. . |
| 0 389 037 | 9/1990 | European Pat. Off. . |
| WO 93/05038 | 3/1993 | WIPO . |
| WO 94/10174 | 5/1994 | WIPO . |
| WO 95/25100 | 9/1995 | WIPO . |

OTHER PUBLICATIONS

Journal of Medicinal Chemistry, vol. 36, No. 25, 1993, pp. 4121–4121, XP000196066, L.M. Gaster et al.
Bioorganic & Medicinal Chemistry Letters, vol. 4, No. 5, 1994, pp. 667–668, XP000196105, L.M. Gaster et al.
Naunyn–Schmiedeberg's Archives of Pharmacology, vol. 349, No. 5, 1994, pp. 546–548, XP000196110, A.J. Kaumann et al.

Primary Examiner—Mukund J. Shah
Assistant Examiner—Ben Schroeder
Attorney, Agent, or Firm—Ellen Ciambrone Coletti

[57] ABSTRACT

The present invention of compounds of formula (I),

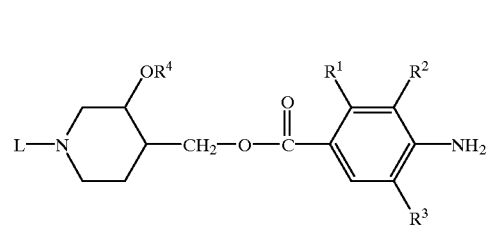

(I)

a stereochemically isomeric form thereof, an N-oxide form thereof or a pharmaceutically acceptable acid addition salt thereof, $R^1$ is $C_{1-6}$alkyloxy, $C_{2-6}$alkenyloxy or $C_{2-6}$alkynyloxy; $R^2$ is hydrogen or $C_{1-6}$alkyloxy, or when taken together $R^1$ and $R^2$ may form a bivalent radical of formula wherein in said bivalent radicals one or two hydrogen atoms may be substituted with $C_{1-6}$alkyl; $R^3$ is hydrogen or halo; $R^4$ is hydrogen or $C_{1-6}$alkyl; L is $C_{3-6}$cycloalkyl, $C_{5-6}$cycloalkanone, $C_{2-6}$alkenyl optionally substituted with aryl, or L is a radical of formula -Alk-$R^5$-, Alk-X—$R^6$, -Alk-Y—C(=O)—$R^8$, or -Alk-Y—C(=O)—$NR^{10}R^{11}$ wherein each Alk is $C_{1-12}$alkanediyl; and $R^5$ is hydrogen, cyano, $C_{1-6}$alkylsulfonylamino, $C_{3-6}$cycloalkyl, $C_{5-6}$cycloalkanone, aryl, di(aryl)methyl or a heterocyclic ringsystem; $R^6$ is hydrogen, $C_{1-6}$alkyl, hydroxy$C_{1-6}$alkyl, $C_{3-6}$cycloalkyl, aryl or heterocyclic ringsystem; X is O, S, $SO_2$ or $NR^7$; said $R_7$ being hydrogen, $C_{1-6}$alkyl or aryl; $R^8$ is hydrogen, $C_{1-6}$alkyl, $C_{3-6}$cycloalkyl, aryl, aryl$C_{1-6}$alkyl, di(aryl)methyl, $C_{1-6}$alkyloxy or hydroxy; Y is $NR^9$ or a direct bond; said $R^9$ being hydrogen, $C_{1-6}$alkyl or aryl $R^{10}$ and $R^{11}$ each independently are hydrogen, $C_{1-6}$alkyl, $C_{3-6}$cycloalkyl, aryl or aryl$C_{1-6}$alkyl, or $R^{10}$ and $R^{11}$ combined with the nitrogen atom bearing $R^{10}$ and $R^{11}$ may form a pyrrolidinyl or piperidinyl ring both being optionally substituted with $C_{1-6}$alkyl, amino or mono or di($C_{1-6}$alkyl) amino, or said $R^{10}$ and $R^{11}$ combined with the nitrogen bearing $R^{10}$ and $R^{11}$ may form a piperazinyl or 4-morpholinyl radical both being optionally substituted with $C_{1-6}$alkyl. Processes for preparing said products, formulations comprising said products and their use as a medicine are disclosed, in particular for treating conditions which are related to impairment of gastric emptying.

9 Claims, No Drawings

ESTERS OF 3-HYDROXY-PIPERIDINEMETHANOL DERIVATIVES

This application is the national stage of application No. PCT/EP97/00584 filed on Feb. 7, 1997, which application claims priority from EP 96200379.4, filed on Feb. 15, 1996.

The present invention is concerned with novel compounds of formula (I) having superior gastrokinetic properties. The invention further relates to methods for preparing such novel compounds, pharmaceutical compositions comprising said novel compounds as well as the use as a medicine of said compounds.

Journal of Medicinal Chemistry, 1993, 36, pp 4121–4123 discloses (1-butyl-4-piperidinyl)methyl-8-amino-7-chloro-1,4-benzodioxane-5-carboxylate hydrochloride, i.e. SB 204070, as a highly potent and selective 5-HT$_4$ receptor antagonist.

Naunyn-Schmiedeberg's Archives of Pharmacology (1994) 349, pp 546–548 discloses (1-butyl-4-piperidinyl) methyl 8-amino-7-iodo-1,4-benzodioxan-5-carboxylate as being a selective and high affinity 5-HT$_4$-receptor antagonist, in particular for human atrial 5-HT$_4$-receptors.

WO 93/05038, published on Mar. 18, 1993 (SmithKline Beecham PLC) discloses a number of substituted 4-piperidinylmethyl 8-amino-7-chloro-1,4-benzodioxan-5-carboxylates having 5 HT$_4$ receptor antagonistic activity.

WO 94/10174, published on May 11, 1994 (SmithKline Beecham PLC) discloses 5-(1-(3-pyridylmethyl)-4-piperidinyl)methyl-8-amino-7-chloro-1,4-benzodioxan-carboxylate, [1-(2-carboethoxyethyl)-4-piperidinyl]methyl-8-amino-7-chloro-1,4-benzodioxan-5-carboxylate, [1-(3-hydroxybutyl)-4-piperidinyl]methyl-8-amino-7-chloro-1,4-benzodioxan-5-carboxylate having 5 HT$_4$ receptor antagonistic activity.

The above prior art documents all disclose substituted 4-piperidinylmethyl 8-amino-7-chloro-1,4-benzodioxan-5-carboxylates and the analogues thereof having 5 HT$_4$ receptor antagonistic activity. Compounds showing 5HT$_4$ antagonism are taught to have potential interest in the treatment of, for example, irritable bowel syndrome, in particular the diarrhoea aspects of irritable bowel syndrome, i.e. these compounds block the ability of 5HT (which stands for 5-hydroxytryptamine, i.e. serotonin) to stimulate gut motility (see WO 93/05038, page 8, lines 12 to 17). The present gastroprokinetic compounds differ in structure mainly by the presence of a hydroxy- or an alkyloxy group on the central piperidine ring.

Bioorganic & Medicinal Chemistry Letters (1994) vol 4, No 5, pp 667–668 discloses oxazolo, oxazino and oxazepino [3,2-a]indole derivatives as being 5 HT$_4$ receptor antagonists.

The present gastroprokinetic compounds differ in structure mainly by the presence of a 2,3,4,5-tetrasubstituted phenylmoiety in stead of the oxazolo, oxazino and oxazepino[3,2-a]indole moiety.

WO 95/25100, published on Sep. 21, 1995, discloses the use of substituted piperidinyl ethyl or propyl 4-amino-5-chloro-2-methoxybenzoic esters as 5 HT$_4$ agonists. The present compounds differ in structure by the different orientation of the central piperidine ring and the different substitution pattern on said piperidine ring.

EP 0 299 566, published on Jan. 18, 1989, discloses N-(3-hydroxy-4-piperidinyl)benzamides having gastrointestinal motility stimulating activity.

EP 0 309 043, published on Mar. 29, 1989, discloses substituted N-(1-alkyl-3-hydroxy-4-piperidinyl)benzamides having gastrointestinal motility stimulating activity.

EP 0 389 037 discloses N-(3-hydroxy-4-piperidinyl) (dihydrobenzofuran, dihydro-2H-benzopyran or dihydrobenzodioxin)carboxamide derivatives as having gastrointestinal motility stimulating activity.

The latter three prior art documents all disclose carboxamide derivatives, while the compounds of the present invention all have an ester function and there is a methylene between the ester oxygen and the piperidine ring.

The problem that this invention sets out to solve is to provide compounds having gastrointestinal motility stimulating properties, particularly having superior gastric emptying activity. Said compounds are also shown to be orally active.

The solution to this problem is provided by the novel compounds of formula (I), that differ structurally from the prior art, inter alia, by the presence of a hydroxy or a $C_{1-6}$alkyloxygroup on the 3 position of the central piperidine ring.

The present invention concerns compounds of formula (I)

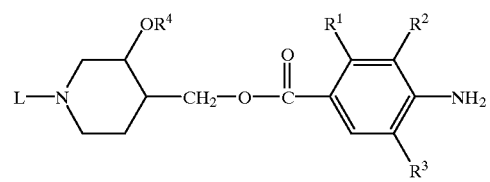

a stereochemically isomeric form thereof, an N-oxide form thereof or a pharmaceutically acceptable acid or base addition salt thereof, wherein $R^1$ is $C_{1-6}$alkyloxy, $C_{2-6}$alkenyloxy or $C_{2-6}$alkynyloxy;

$R^2$ is hydrogen or $C_{1-6}$alkyloxy, or taken together $R^1$ and $R^2$ may form a bivalent radical of formula

| —O—CH$_2$—O— | (a-1), |
|---|---|
| —O—CH$_2$—CH$_2$— | (a-2), |
| —O—CH$_2$—CH$_2$—O— | (a-3), |
| —O—CH$_2$—CH$_2$—CH$_2$— | (a-4), |
| —O—CH$_2$—CH$_2$—CH$_2$—O— | (a-5), |
| —O—CH$_2$—CH$_2$—CH$_2$—CH$_2$— | (a-6), | wherein in said bivalent radicals one or two hydrogen atoms may be substituted with $C_{1-6}$alkyl, $R^3$ is hydrogen or halo;

$R^4$ is hydrogen or $C_{1-6}$alkyl;

L is $C_{3-6}$cycloalkyl, $C_{5-6}$cycloalkanone, $C_{2-6}$alkenyl optionally substituted with aryl, or L is a radical of formula

| -Alk-R$^5$ | (b-1), |
|---|---|
| -Alk-X—R$^6$ | (b-2), |
| -Alk-Y—C(=O)—R$^8$ | (b-3), | or

| -Alk-Y—C(=O)—NR$^{10}$R$^{11}$ | (b-4), | wherein each Alk is $C_{1-12}$alkanediyl; and $R^5$ is hydrogen, cyano, $C_{1-6}$alkylsulfonylamino, $C_{3-6}$cycloalkyl, $C_{5-6}$cycloalkanone, aryl, di(aryl)methyl or Het$^1$;

$R^6$ is hydrogen, $C_{1-6}$alkyl, hydroxy$C_{1-6}$alkyl, $C_{3-6}$cycloalkyl, aryl or Het$^2$;

X is O, S, SO$_2$ or NR$^7$; said $R^7$ being hydrogen, $C_{1-6}$alkyl or aryl;

$R^8$ is hydrogen, $C_{1-6}$alkyl, $C_{3-6}$cycloalkyl, aryl, aryl$C_{1-6}$alkyl, di(aryl)methyl, $C_{1-6}$alkyloxy or hydroxy;

Y is NR$^9$ or a direct bond; said $R^9$ being hydrogen, $C_{1-6}$alkyl or aryl;

$R^{10}$ and $R^{11}$ each independently are hydrogen, $C_{1-6}$alkyl, $C_{3-6}$cycloalkyl, aryl or aryl$C_{1-6}$alkyl, or $R^{10}$ and $R^{11}$ combined with the nitrogen atom bearing $R^{10}$ and $R^{11}$ may form a pyrrolidinyl or piperidinyl ring both being optionally substituted with $C_{1-6}$alkyl, amino or mono or di($C_{1-6}$alkyl)amino, or said $R^{10}$ and $R^{11}$ combined with the nitrogen bearing $R^{10}$ and $R^{11}$ may form a piperazinyl or 4-morpholinyl radical both being optionally substituted with $C_{1-6}$alkyl;

each aryl being unsubstituted phenyl or phenyl substituted with 1, 2 or 3 substituents each independently selected from halo, hydroxy, $C_{1-6}$alkyl, $C_{1-6}$alkyloxy, aminosulfonyl, $C_{1-6}$alkylcarbonyl, nitro, trifluoromethyl, amino or aminocarbonyl; and Het$^1$ and Het$^2$ each independently are selected from furan; furan substituted with $C_{1-6}$alkyl or halo; tetrahydrofuran; a tetrahydrofuran substituted with $C_{1-6}$alkyl; a dioxolane; a dioxolane substituted with $C_{1-6}$alkyl, a dioxane; a dioxane substituted with $C_{1-6}$alkyl; tetrahydropyran; a tetrahydropyran substituted with $C_{1-6}$alkyl; pyrrolidinyl; pyrrolidinyl substituted with one or two substituents each independently selected from halo, hydroxy, cyano, or $C_{1-6}$alkyl; pyridinyl; pyridinyl substituted with one or two substituents each independently selected from halo, hydroxy, cyano, $C_{1-6}$alkyl; pyrimidinyl; pyrimidinyl substituted with one or two substituents each independently selected from halo, hydroxy, cyano, $C_{1-6}$alkyl, $C_{1-6}$alkyloxy, amino and mono and di($C_{1-6}$alkyl)amino; pyridazinyl; pyridazinyl substituted with one or two substituents each independently selected from hydroxy, $C_{1-6}$alkyloxy, $C_{1-6}$alkyl or halo; pyrazinyl; pyrazinyl substituted with one ore two substituents each independently selected from halo, hydroxy, cyano, $C_{1-6}$alkyl, $C_{1-6}$alkyloxy, amino, mono- and di($C_{1-6}$alkyl)amino and $C_{1-6}$alkyloxycarbonyl;

Het$^1$ can also be a radical of formula

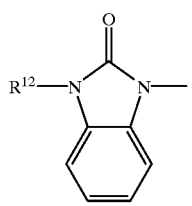

(c-1)

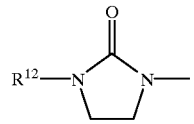

(c-2)

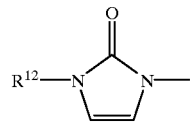

(c-3)

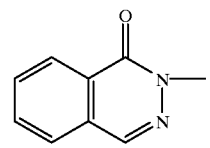

(c-4)

Het$^1$ and Het$^2$ each independently can also be selected from the radicals of formula

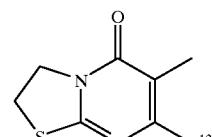

(d-1)

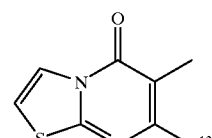

(d-2)

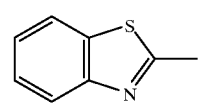

(d-3)

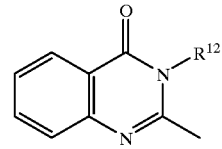

(d-4)

$R^{12}$ and $R^{13}$ each independently are hydrogen or $C_{1-4}$alkyl.

As used in the foregoing definitions halo is generic to fluoro, chloro, bromo and iodo; $C_{1-4}$alkyl defines straight and branched chain saturated hydrocarbon radicals having from 1 to 4 carbon atoms such as, for example, methyl, ethyl, propyl, butyl, 1-methyl-ethyl, 2-methylpropyl and the like; $C_{1-6}$alkyl is meant to include $C_{1-4}$alkyl and the higher homologues thereof having 5 or 6 carbon atoms, such as, for example, 2-methyl-butyl, pentyl, hexyl and the like; $C_{3-6}$cycloalkyl is generic to cyclopropyl, cyclobutyl, cyclopentyl and cyclohexyl; $C_{2-6}$alkenyl defines straight and branched chain unsaturated hydrocarbon radicals having from 2 to 6 carbon atoms, such as ethenyl, propenyl, butenyl, pentenyl or hexenyl; $C_{2-6}$alkynyl defines straight and branched chain hydrocarbon radicals having 2 to 6 atoms containing a triple bond, such as ethynyl, propynyl, butynyl, pentynyl or hexynyl; $C_{1-12}$alkanediyl defines bivalent straight or branched chain hydrocarbon radicals containing from 1 to 12 carbon atoms such as, for example, 1,2-ethanediyl, 1,3-propanediyl, 1,4-butanediyl, 1,5-pentanediyl, 1,6-hexanediyl, 1,7-heptanediyl, 1,8-octanediyl, 1,9-nonanediyl, 1,10-decanediyl, 1,11-undecanediyl, 1,12-dodecanediyl and the branched isomers thereof. $C_{1-6}$alkanediyl is defined in an analogous way as $C_{1-12}$alkanediyl.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of formula (I) are obviously intended to be embraced within the scope of this invention.

The pharmaceutically acceptable acid addition salts as mentioned hereinabove are meant to comprise the therapeutically active non-toxic acid addition salt forms which the compounds of formula (I) are able to form. The latter can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the amnmonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds of formula (I) as well as the salts thereof, are able to form. Such solvates are for example hydrates, alcoholates and the like.

Some of the compounds of formula (I) may also exist in their tautomeric form. Such forms although not explicitly indicated in the above formula are intended to be included within the scope of the present invention. For instance, when an aromatic heterocyclic ring is substituted with hydroxy the keto-form may be the mainly populated tautomer.

The N-oxide forms of the compounds of formula (I), which may be prepared in art-known manners, are meant to comprise those compounds of formula (I) wherein one or several nitrogen atoms are oxidized to the so-called N-oxide. Particularly those N-oxides are envisaged wherein the piperidine-nitrogen is N-oxidized.

$R^1$ is suitably methoxy and $R^2$ is hydrogen;

when taken together $R^1$ and $R^2$ suitably form a radical of formula (a-1), (a-2), (a-3), (a-4) or (a-5), wherein optionally one or two hydrogen atoms are substituted with methyl;

$R^3$ is suitably fluoro, chloro or bromo;

$R^4$ is suitably hydrogen or methyl.

Interesting compounds are those compounds of formula (I) wherein $R^1$ is methoxy, $R^2$ is hydrogen and $R^3$ is chloro.

Also interesting compounds are those compounds of formula (I) wherein $R^1$ and $R^2$ taken together form a radical of formula (a-2), (a-3) or (a-4).

More interesting compounds are those interesting compounds of formula (I) wherein $R^4$ is hydrogen or methyl.

Particular compounds are those more interesting compounds with the trans configuration, i.e. the hydroxy or methoxy is in the trans position in relation to the methylene on the central piperidine moiety.

Very particular compounds are those compounds wherein L is:

$C_{2-6}$alkenyl, especially butenyl;

a radical of formula (b-1), wherein each Alk is $C_{1-6}$alkanediyl, and $R^5$ is hydrogen, cyano, $C_{1-6}$alkylsulfonylamino, $C_{3-6}$cycloalkyl or Het$^1$, Het$^1$ being tetrahydrofuran, dioxolane substituted with $C_{1-6}$alkyl, or a radical of formula (c-3) or a radical of formula (d-1);

a radical of formula (b-2), wherein each Alk is $C_{1-6}$alkanediyl, X being O or NR$^7$ wherein R$^7$ is hydrogen and $R^6$ is hydrogen, $C_{1-6}$alkyl, hydroxy$C_{1-6}$alkyl, $C_{3-6}$cycloalkyl, aryl or Het$^2$, aryl being phenyl or phenyl substituted with halo, Het$^2$ being pyridinyl; pyridinyl substituted with cyano; pyridazinyl substituted with one or more substituents selected from hydroxy, halo and $C_{1-6}$alkyl; pyrazinyl substituted with $C_{1-6}$alkyl;

a radical of formula (b-3) wherein Y is a direct bond, and $R^8$ is $C_{1-6}$alkyl or $C_{1-6}$alkyloxy; a radical of formula (b-4) wherein Y is a direct bond, and $R^{10}$ and $R^{11}$ combined with the nitrogen atom bearing $R^{10}$ and $R^{11}$ form a pyrrolidinyl.

Particularly interesting compounds are those compounds wherein L is butyl, methoxypropyl, methylcarbonylpropyl, hydroxyethoxyethyl, 2-[2-methyl-1,3-dioxolane]propyl, ethyl substituted with 4-methyl-2-pyridazinon, ethyl substituted with 4-chloro-2-pyridazinon, propyl with 4-methyl-2-pyridazinon, or propyl with 4-chloro-2-pyridazinon.

Preferred compounds are trans-(1-butyl-3-hydroxy-4-piperidinyl]methyl 4-amino-5-chloro-2,3-dihydro-7-benzofurancarboxylate;

trans-[3-hydroxy-1-[2-(2-hydroxyethoxy)ethyl]-4-piperidinyl]methyl 8-amino-7-chloro-2,3-dihydro-1,4-benzodioxin-5-carboxylate;

trans-[3-hydroxy-1-[3-(2-methyl-1,3-dioxolan-2-yl)propyl]-4-piperidinyl]methyl 8-amino-7-chloro-2,3-dihydro-1,4-benzodioxin-5-carboxylate;

trans-[3-hydroxy-1-(3-methoxypropyl)-4-piperidinyl] methyl 8-amino-7-chloro-2,3-dihydro-1,4-benzodioxin-5-carboxylate ethanedioate(1:1);

trans-[3-hydroxy-1-(3-methoxypropyl)-4-piperidinyl] methyl 4-amino-5-chloro-2,3-dihydro-7-benzofurancarboxylate;

trans-[3-hydroxy-1-[3-(2-methyl-1,3-dioxolan-2-yl) propyl)-4-piperidinyl]methyl 4-amino-5-chloro-2,3-dihydro-7-benzofurancarboxylate;

trans-[3-hydroxy-1-(4-oxopentyl)-4-piperidinyl]methyl 4-amino-5-chloro-2,3-dihydro-7-benzofurancarboxylate; and trans-[1-[2-(1,6-dihydro-3-methyl-6-oxo-1-pyridazinyl) ethyl]-3-hydroxy-4-piperidinyl]methyl 4-amino-5-chloro-2,3-dihydro-2,2-dimethyl-7-benzofurancarboxylate; the stereochemically isomeric forms thereof and the pharmaceutically acceptable acid addition salts thereof.

Most preferred is (±)-trans-(1-butyl-3-hydroxy-4-piperidinyl)methyl 8-amino-7-chloro-2,3-dihydro-1,4-benzodioxin-5-carboxylate, a pharmaceutically acceptable acid addition salt thereof or a stereoisomeric form thereof. Especially, the laevo-rotatory isomer of trans-(1-butyl-3-hydroxy-4-piperidinyl)methyl 8-amino-7-chloro-2,3-dihydro-1,4-benzodioxin-5-carboxylate is most preferred.

The compounds of formula (I) may be prepared by reacting an intermediate of formula (II) with an carboxylic acid derivative of formula (III) or a reactive functional derivative thereof, such as for example carbonyl imidazole derivatives. Said esterbond formation may be performed by stirring the reactants in an appropriate solvent in the presence of a base, such as sodium imidazolide.

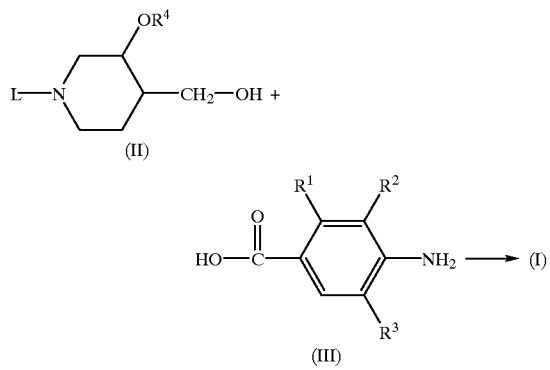

Another way of preparing compounds of formula (I) is by N-alkylating an intermediate of formula (IV), wherein W represents an appropriate leaving group such as halo, with a reagent of formula (V). Said N-alkylation reaction may be performed by stirring the reactants in an appropriate solvent. Optionally a base may be present.

Alternatively, an intermediate of formula (V) is reductively N-alkylated with an appropriate ketone or aldehyde intermediate of formula L'=O (VI), said L'=O being a compound of formula L-H, wherein two geminal hydrogen atoms in the $C_{1-12}$alkanediyl moiety are replaced by =O, with a piperidine of formula (V).

Further, compounds of formula (I) may be prepared by carbonylation of an intermediate of formula (XIII), wherein X is bromo or iodo, in the presence of an intermediate of formula (II).

Said carbonylation reaction is carried out in a reaction-inert solvent such as, e.g. acetonitrile or tetrahydrofuran, in the presence of a suitable catalyst and a tertiary amine such as, e.g. triethylamine, and at a temperature ranging between room temperature and the reflux temperature of the reaction mixture. Suitable catalysts are, for instance, palladium (triphenylphosphine) complexes. Carbon monoxide is administered at atmospheric pressure or at an increased pressure. Analogous carbonylation reactions are described in Chapter 8 of "Palladium reagents in organic syntheses", Academic Press Ltd., Benchtop Edition 1990, by Richard F. Heck; and the references cited therein.

Said ester formation reaction is known from the above mentioned reference with metal catalysts which are soluble such as palladium(triphenylphosphine) complexes. Unexpectedly, we have found that these reactions can also be performed on metal catalysts which are insoluble or immobilized on a solid carrier. Suitable catalysts are for example palladium-on-carbon, Raney nickel or $Cu_2O$. These insoluble catalysts or catalysts on a solid phase are much less expensive than the metal complexes and are often much easier to handle when synthesis is done on an industrial scale.

In other words, we deem to have found a novel and inventive way to prepare esters in the following way:

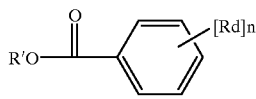

In the above formulas Rd represent any substituent possible on a phenyl, n is an integer from 1 to 5, and R'O is the alcohol-rest of any alcohol. In other words, R'OH can be any alcohol. The term halide suitably refers to chloro, bromo, iodo. Preferred halides are bromo and iodo.

The preferred catalyst is palladium-on-carbon.

The pressure of CO, i.e. carbon monoxide, may vary widely and a person skilled in the art will certainly be able to find the suitable range after straightforward experimentation. The preferred pressure of CO, i.e. carbon monoxide, is 50 kg/cm$^2$ (about $4.9 \times 10^6$ Pa). It may suitably range between about 1 kg/cm$^2$ (about $1 \times 10^5$ Pa) and about 100 kg/cm$^2$ (about $10 \times 10^6$ Pa).

The reaction temperature may range from room temperature and the reflux temperature of the reaction mixture.

This reaction is preferably performed in a solvent, which can be in the alcohol R'OH, itself or in acetonitrile or in tetrahydrofuran. Preferred solvent is acetonitrile. Depending upon the solvent side-reactions may occur. In acetonitrile, few side-products were formed.

Suitably a base is also present. An interesting base is for instance triethylamine.

Preferably said alcohol is a primary alcohol, more preferably R'OH is a primary alcohol.

The preparation of esters of formula (I) as shown hereinabove is a preferred embodiment of said novel and inventive way of preparing esters.

An intermediate of formula (V) may be prepared by reacting an intermediate of formula (VII), wherein PG represents an appropriate protective group, such as for example a t-butoxycarbonyl or a benzyl group or a photoremovable group, with an acid of formula (III) or an appropriate reactive functional derivative thereof, and subsequent deprotection of the thus formed intermediate, i.e. removal of PG by art-known methods.

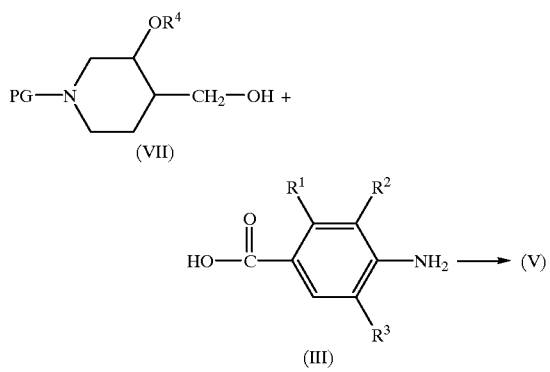

An intermediate of formula (VII), wherein R$^4$ is a hydrogen and PG is a benzyl group, having the trans configuration, is known from J. Med. Chem. 1973, 156.

An intermediate of formula (II) may be prepared by reacting an intermediate of formula (VIII), with an intermediate of formula (IV). Said intermediate of formula (VIII) may be prepared by deprotection of an intermediate of formula (VII). Some of the intermediates of formula (VII) are art-known. For instance cis-3-hydroxy-4-hydroxymethylpiperidine is known from J.Org. Chem, 1969, 34(11), 3674.

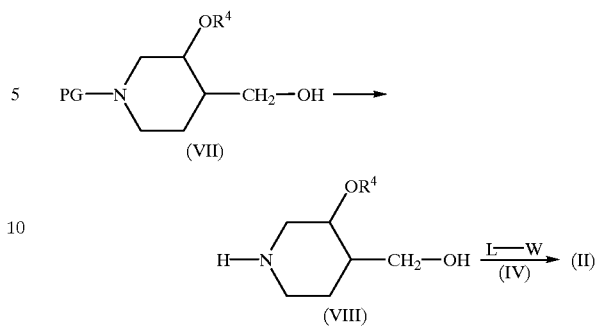

In some cases, it may be appropriate to protect the primary alcohol functionality during the reactionsequence starting from intermediate (VII) to intermediate (II). Protecting groups for primary alcohol functionalities are art-known. These protecting groups may then be removed at the appropriate time during the further synthesis.

The intermediates of formula (VII) wherein R$^4$ is C$_{1-6}$alkyl and having the cis configuration can be prepared by hydrogenating an intermediate of formula (IX) following art-known methods.

In intermediate (IX), PG is as defined hereinabove while PG' is a protective group which is preferably removable by hydrogenation, such as, for example, a benzyl group.

The intermediate (IX) can be prepared by reacting a protected piperidone of formula (X) with a phosphonium reagent of formula [(aryl)$_3$P—CH$_2$—O—PG']$^+$-halide$^-$, in appropriate conditions for carrying out a Wittig-type reaction.

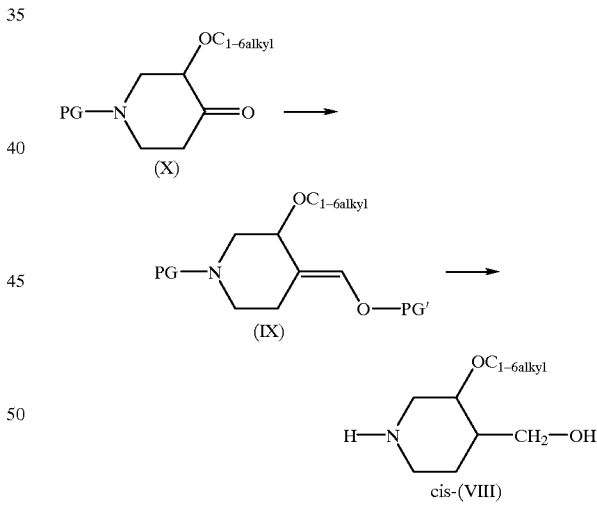

The intermediates of formula trans-(VIII) having R$^4$ being C$_{1-6}$alkyl may be prepared by alkylating the intermediates of formula trans-(VIII) wherein R$^4$ is hydrogen, which may be prepared as shown hereinunder.

A novel way of preparing an intermediate of formula (VII) having the trans-configuration was found. Said novel preparation starts from an intermediate of formula (XI) having the cis-configuration or from an intermediate of formula (XII) having the cis-configuration. In said intermediates of formula (XI) and (XII) PG is as defined above, R$^{4a}$ is hydrogen, C$_{1-6}$alkyl or a protective group such as for example, benzyl, t-butoxycarbonyl and the like.

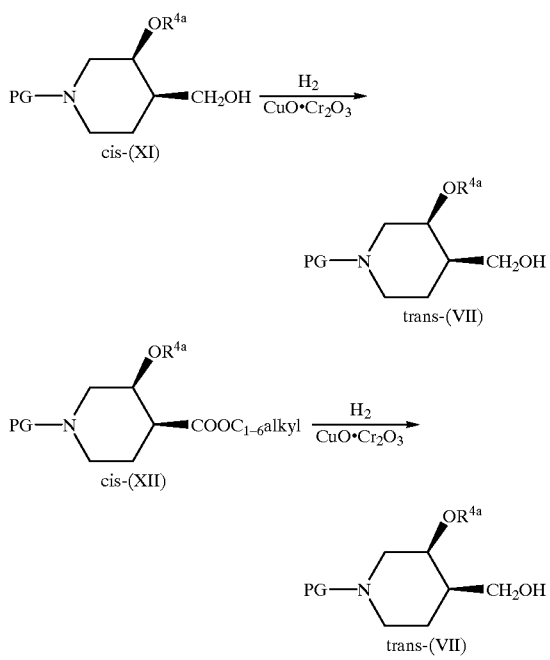

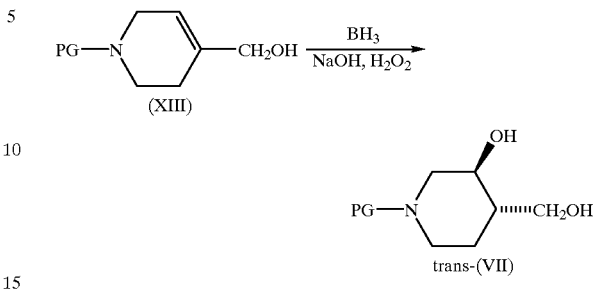

Said inversion-reaction is carried out in an appropriate solvent, such as, for example an ether, e.g. tetrahydrofuran in the presence of $CuO.Cr_2O_3$ under a hydrogen atmosphere and in the presence of an appropriate base, such as, for example calciumoxide.

The preferred hydrogen pressure and reaction temperature is dependent upon the starting material. Starting from cis-(XI) the hydrogen pressure preferably ranges from 900 to 2000 kPa (measured at room temperature) and the reaction temperature ranges from room temperature up to 200° C., preferably the reaction temperature is about 120° C.

When starting from cis-(XII), the preferred hydrogen pressure range is from 1500 kPa to 2200 kPa, preferably between 1800 kPa to 2000 kPa. The reaction temperature is between 100° C. and 200° C. preferably at about 125° C. Apparently an equilibrium is reached, typically with a diastereomeric ratio of about 65:35 (trans:cis) as determined by gas chromatography. However via recrystallization it is possible to purify the desired trans-isomer. A suitable solvent for recrystallization is an ether, e.g. diisopropyl ether.

The pure intermediate of formula (VIII) having the trans configuration can also be obtained by chromatographic techniques, such as, for example gravitation chromatography or (H)PLC.

Still another novel way of preparing intermediates of formula trans-(VIII) is to react an intermediate of formula (XIII) with borane or a borane derivative. Borane itself is commercially available as a borane-tetrahydrofuran complex. Borane derivatives, especially chiral borane derivatives are also commercially available. The reaction with borane is performed in a reaction inert solvent, preferable an ether, e.g. tetrahydrofuran. While adding the borane or the borane derivative the reaction mixture is kept at temperatures below 0° C., interestingly at a temperature below −50° C. and preferably at a temperature of about −70° C. After adding the borane or the borane derivative to the reaction mixture the mixture is allowed to heat up while stirring is continued. The mixture is stirred for several hours. Subsequently, a hydroxide, e.g. sodium hydroxide is added as well as a peroxide, e.g. hydrogen peroxide and the reaction mixture is stirred at elevated temperatures for several hours. After this treatment the reaction product was isolated in art-known manner.

The compounds of formula (I), the N-oxide forms, the pharmaceutically acceptable salts and stereoisomeric forms thereof possess favourable intestinal motility stimulating properties. In particular the present compounds show significant gastric emptying activity as is evidenced in pharmacological example P-2, the "Gastric emptying of an acaloric liquid meal delayed by administration of lidamidine in conscious dogs"-test. Moreover, the compounds of the present invention also show an improvement of the gastrointestinal motility as is evidenced in pharmacological example P-1: "Telemetric recording of motility of the antrum, pylorus and duodenum in the conscious dog"-test.

The compounds of formula (I) also are shown to have a beneficial effect such as increase of basal pressure of the LES, i.e. Lower Esophageal Sphincter.

Most of the intermediates of formula (V) have shown to have analogous activity as the final compounds of formula (I).

In view of the capability of the compounds of the present invention to enhance the gastrointestinal motility, and in particular to activate gastric emptying, the subject compounds are useful to treat conditions related to a hampered or impaired gastric emptying and more generally to treat conditions related to a hampered or impaired gastrointestinal transit.

In view of the utility of the compounds of formula (I), it follows that the present invention also provides a method of treating warm-blooded animals, including humans (generally called herein patients) suffering from conditions related to a hampered or impaired gastric emptying or more generally suffering from conditions related to a hampered or impaired gastrointestinal transit. Consequently a method of treatment is provided for relieving patients suffering from conditions, such as, for example, gastroesophageal reflux, dyspepsia, gastroparesis, constipation, post-operative ileus, and intestinal pseudo-obstruction. Gastroparesis can be brought about by an abnormality in the stomach or as a complication of diseases such as diabetes, progressive systemic sclerosis, anorexia nervosa and myotonic dystrophy. Constipation can result from conditions such as lack of intestinal muscle tone or intestinal spasticity. Post-operative ileus is an obstruction or a kinetic impairment in the intestine due to a disruption in muscle tone following surgery. Intestinal pseudo-obstruction is a condition characterized by constipation, colicky pain, and vomiting, but without evidence of physical obstruction. The compounds of the present invention can thus be used either to take away the actual cause of the condition or to relief the patients from symptoms of the conditions. Dyspepsia is an impairment of the function of digestion, that can arise as a symptom of a primary gastrointestinal dysfunction, especially a gastrointestinal dysfunction related to an increased muscle tone or as a complication due to other disorders such as appendicitis, galbladder disturbances, or malnutrition.

The symptoms of dyspepsia may also arise due to the intake of chemical substances, e.g. SSRI's.

Some of the compounds also additionally show stimulating kinetic activity on the colon.

The compounds of formula (I) and of formula (V) are cardio haemodynamically and cardio electrophysiologically safe.

Hence, the use of a compound of formula (I) as medicine is provided, and in particular the use of a compound of formula (I) for the manufacture of a medicine for treating conditions involving a decreased motility of the stomach. Both prophylactic and therapeutic treatment are envisaged.

To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In general it is contemplated that a therapeutically effective amount would be from about 0.001 mg/kg to about 10 mg/kg body weight, preferably from about 0.02 mg/kg to about 5 mg/kg body weight. A method of treatment may also include administering the active ingredient on a regimen of between two or four intakes per day.

Experimental Part

In the procedures described hereinafter the following abbreviations were used : "THF", which stands for tetrahydrofuran; "DIPE" stands for diisopropylether; "EtOAc" stands for ethyl acetate; "$NH_4Oac$" stands for ammonium acetate; "HOAc" stands for acetic acid.

For some chemicals the chemical formula was used, e.g. NaOH for sodium hydroxide, $K_2CO_3$ for potassium carbonate, $H_2$ for hydrogen gas, $CH_3CN$ for acetonitrile, $MgSO_4$ for magnesium sulfate, $CuO.Cr_2O_3$ for copper chromite, $N_2$ for nitrogen gas, $CH_2Cl_2$ for dichloromethane, $CH_3OH$ for methanol, $NH_3$ for ammonia, HCl for hydrochloric acid, NaH for sodium hydride, $CaCO_3$ for calcium carbonate, CO for carbon monoxide, KOH for potassium hydroxide.

Preparation of the Intermediates

EXAMPLE I-1 a) A mixture 1,2,3,6-tetrahydro-1-(phenylmethyl)-4-pyridinemethanol (0.367 mol) and THF (1000 ml) was stirred at −70° C. and a solution of borane in THF (1 M) was added dropwise thereto. After the addition, the reaction mixture was allowed to warm up to room temperature and stirred at room temperature for 18 h. The reaction mixture was cooled to −10° C. and water (23 ml) was added dropwise, NaOH (3M in water, 18 ml) was added dropwise and hydrogen peroxide (30% solution in water, 28 ml) was added dropwise at the same time. Then, simultaneously, NaOH (3M in water, 36 ml) and the hydrogen peroxide (30% solution in water, 29 ml) was added dropwise. Again NaOH (50% in water, 80 ml) was added. The reaction mixture was stirred at reflux for 4 hours. The reaction mixture was cooled and filtered. The filtrate was evaporated. The resulting precipitate was dissolved in water (500 ml) and saturated with $K_2CO_3$. The product was extracted with $CH_2Cl_2$. The resulting solution was dried over $MgSO_4$ and evaporated. The residue was crystallized from DIPE/ $CH_3CN$. After several crystallizations a total yield of 40, 8 g of (±)-trans-1-(phenylmethyl)-3-hydroxy-4-piperidinemethanol was obtained (Yield: 50.1%).

b) A mixture of (±)-trans-1-(phenylmethyl)-3-hydroxy-4-piperidinemethanol (17.8 g, 0.085 mol) (already described in J. Med. Chem., 1973, 156) in methanol (250 ml) was hydrogenated, at 50° C., with palladium on activated carbon (10%) (2 g) as a catalyst. After uptake of $H_2$ (1 equiv.), the catalyst was filtered off and the filtrate was evaporated, yielding 12 g of (±)-trans-3-hydroxy-4-piperidinemethanol (interm. 1-a) (quantitative yield; used in next reaction step, without further purification). The corresponding cis-isomer is known from J. Org. Chem., 1969, 34 (11).

A mixture of intermediate (1-a) (0.022 mol) and butanal (0.025 mol) in methanol (150 ml) was hydrogenated with palladium on activated carbon (10%) (1 g) as a catalyst in the presence of a solution of thiophene (4% in THF) (1 ml). After uptake of $H_2$ (1 equiv.), the catalyst was filtered off and the filtrate was evaporated, yielding 4.1 g of (±)-trans-1-butyl-3-hydroxy-4-piperidinemethanol (interm. 1-b) (99.5%, used in next reaction step without further purification).

The corresponding cis-isomer was prepared in an analogous manner:

TABLE I-1

[Structure: piperidine ring with OR⁴ at position 3, CH₂OH at position 4, and L—N at position 1]

| Interm. No. | L | OR⁴ | physical data |
|---|---|---|---|
| I-c | $CH_3(CH_2)_3$— | OH | cis |
| I-d | $CH_3CH_2$— | $OCH_3$ | cis |

EXAMPLE I-2 a) A mixture of (±)-cis-1-(phenylmethyl)-3-hydroxy-4-piperidinemethanol (0.11 mol) and calcium oxide (5 g) in tetrahydrofuran (250 ml) was hydrogenated with copper chromite ($CuO.Cr_2O_3$) (4 g) as a catalyst at 120° C. The catalyst was filtered off and the filtrate was evaporated. The residue was purified by column chromatography ($CH_2Cl_2$/ $CH_3OH/CH_3OH(NH_3)$: 93/5/2). The fractions were evaporated, yielding 8.5 g of (±)-cis-1-(phenylmethyl)-3-hydroxy-4-piperidinemethanol and 6.32 g of (±)-trans-1-(phenylmethyl)-3-hydroxy-4-piperidinemethanol.

b) A mixture of ethyl (±)-cis-1-(phenylmethyl)-3-hydroxy-4-piperidinecarboxylic acid (40 g) (90% cis; 10% trans) (0.15 mol) and calcium oxide (10 g) in tetrahydrofuran (500 ml) was hydrogenated with copper chromite ($CuO.Cr_2O_3$) (10 g) as a catalyst at 125° C. After uptake of hydrogen, the catalyst was filtered off and the filtrate was evaporated. The residue was solidified and crystallized twice in DIPE. The residue was filtered off and dried in vacuo at 40° C., yielding 16 g of (±)-trans-1-(phenylmethyl)-3-hydroxy-4-piperidinemethanol (96% trans and 3% cis).

EXAMPLE I-3 a) Reaction under $N_2$ flow. A suspension of triphenyl [(phenylmethoxy)methyl] phosphonium chloride (0.18 mol) in THF (600 ml) was stirred and cooled to −75° C. A solution of n-butyl lithium in hexanes 2.5 M (0.18 mol) was added dropwise at −75° C. The mixture was stirred for 90 minutes at −75° C. A suspension of 3-methoxy-1-(phenylmethyl)-4-piperidone (0.12 mol) in THF (180 ml) was added at −75° C. and the resulting reaction mixture was allowed to warm to room temperature. The reaction mixture was stirred for one hour at room temperature. The mixture was filtered and the filtrate was evaporated. The residue was dissolved in $CH_2Cl_2$, and purified by column chromatography over silica gel (eluent: EtOAc/hexane 30/70). Two desired fractions were collected and the solvent was evaporated, yielding 4 g of fraction 1 (10.3%) and 17 g of fraction 2. Fraction 2 was purified by column chromatography over silica gel (eluent: hexane/EtOAc 80/20). The desired fractions were collected and the solvent was evaporated, yielding 13 g (33.5%) of (±)-3-methoxy-4-[(phenylmethoxy)-methylene]-1-(phenylmethyl)piperidine (interm. 3a).

b) A mixture of intermediate (3a) (0.043 mol) in THF (250 ml) was hydrogenated with platinum on activated carbon (5%) (3 g) as a catalyst. After uptake of $H_2$ (1equiv.), the catalyst was filtered off and the filtrate was evaporated. The residue was purified by high-performance liquid chromatography over LiChroprep RP-18® (750 g; 8 cm; DAC column; eluent A: (0.5% $NH_4OAc$ in $H_2O$)/$CH_3OH$ 75/25; eluent B: $CH_3CN$; step gradient). The pure fractions were collected and the solvent was evaporated, yielding 8.34 g (59.6%) of (±)-3-methoxy-4-[(phenylmethoxy)methyl]-1-(phenylmethyl)-piperidine (interm. 3b).

c) A mixture of intermediate (3b) (0.0256 mol) in THF (250 ml) was hydrogenated with palladium on activated carbon (10%) (2 g) as a catalyst. After uptake of $H_2$ (1 equiv.), bis (1,1-dimethylethyl) dicarbonate (0.0256 mol) was added and hydrogenation was continued. After uptake of $H_2$ (1 equiv.), the catalyst was filtered off and the filtrate was evaporated. The residue was purified by column chromatography over silica gel (eluent: $CH_2Cl_2/CH_3OH$ 95/5). The desired fractions were collected and the solvent was evaporated. The residue was solidified and crystallized from petroleum ether (2×). The precipitate was filtered off and dried (vacuum; 30° C.), yielding 2.6 g (40%) of (±)-1,1-dimethylethyl cis-4-(hydroxymethyl)-3-methoxy-1-piperidine-carboxylate (interm. 3c).

d) A mixture of intermediate (3c) (0.04 mol) in a mixture of HCl in diethyl ether (25 ml) and methanol (250 ml) was stirred and refluxed for 30 minutes. The reaction mixture was cooled and the solvent was evaporated. Toluene was added and azeotroped on the rotary evaporator, yielding 8 g (90%) of (±)-cis-methoxy-4-piperidinemethanol hydrochloride (interm. 3d).

e) A mixture of intermediate (3d) (0.04 mol), potassium acetate (5 g) and butanal (0.04 mol) in methanol (150 ml) was hydrogenated with palladium on activated carbon (10%) (2 g) as a catalyst in the presence of thiophene (4% in THF) (1 ml). After uptake of $H_2$ (1 equiv.), the catalyst was filtered off and the filtrate was evaporated. The residue was dissolved in $CH_2Cl_2/(CH_3OH/NH_3)$ and purified by short column chromatography over silica gel (eluent: $CH_2Cl_2/$ $(CH_3OH/NH_3)$ 95/5). The desired fractions were collected and the solvent was evaporated, yielding 7.2 g (>90%) of (±)-cis-1-butyl-3-methoxy-4-piperidinemethanol (interm. 3e).

EXAMPLE I-4

4a) A mixture of (tetrahydro-2-furanyl)methyl methanesulfonate (0.05 mol), intermediate (3d) (0.046 mol) and N,N-diethylethanamine (0.12 mol) in N,N-dimethylformamide (150 ml) was stirred for 20 hours at 60° C. More (tetrahydro-2-furanyl)-methyl methanesulfonate (0.01 mol) was added and the resulting reaction mixture was stirred for 4 hours at 60° C. The reaction mixture was cooled and the solvent was evaporated. The residue was purified by column chromatography over silica gel (eluent: $CH_2Cl_2/(CH_3OH/$ $NH_3)$ 95/5). The pure fractions were collected and the solvent was evaporated, yielding 3.1 g (32%) of (±)-cis-1-(2-amonoethyl)-3-hydroxy-4-piperidinemethanol (interm. 4a).

The following intermediates, as depicted in table I-2, were prepare according to this method.

TABLE I-2
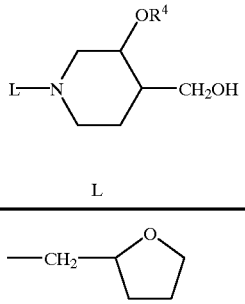
| Interm. No. | OR⁴ | L | physical data |
|---|---|---|---|
| 4-a | OCH₃ | 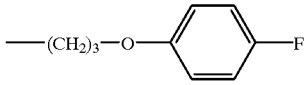 | cis |
| 4-b | OCH₃ | 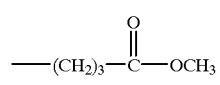 | cis |
| 4-c | OH | —(CH₂)₃—CN | trans |
| 4-d | OH | 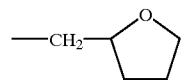 | trans |
| 4-e | OH | 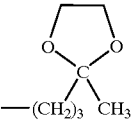 | cis |
| 4-f | OH | 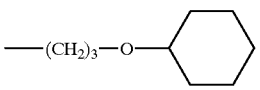 | cis |
| 4-g | OH | —(CH₂)₃—O—CH₃ | trans |
| 4-h | OH | 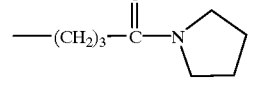 | cis |
| 4-i | OH | —(CH₂)₃—CN | cis |
| 4-j | OH | 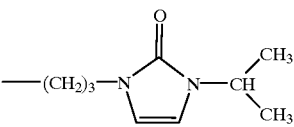 | cis |
| 4-k | OH | 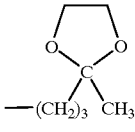 | cis |
| 4-l | OH | 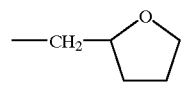 | trans |
| 4-m | OH | —(CH₂)₂—NH—SO₂—CH₃ | trans |
| 4-n | OH |  | trans |

TABLE I-2-continued

[Structure: piperidine with OR⁴ at 3-position, CH₂OH at 4-position, L—N at 1-position]

| Interm. No. | OR⁴ | L | physical data |
|---|---|---|---|
| 4-o | OH | —(CH₂)₂—N(pyridazin-3(2H)-one-6-methyl) | 103–104° C., trans |
| 4-p | OH | —(CH₂)₃—O—CH₃ | cis |
| 4-q | OH | —(CH₂)₂—N(pyridazin-3(2H)-one-6-methyl) | 131–132° C., cis |
| 4-r | OH | —(CH₂)₃—O—(4-fluorophenyl) | trans |
| 4-s | OH | —(CH₂)₂—N(imidazolidin-2-one-N'-ethyl) | trans |
| 4-t | OH | —(CH₂)₂—(7-methyl-5-oxo-2,3-dihydro-5H-thiazolo[3,2-a]pyrimidin-6-yl) | cis |
| 4-u | OH | —(CH₂)₃—CH(4-fluorophenyl)₂ | trans |
| 4-v | OH | —(CH₂)₃—C(=O)—N(pyrrolidinyl) | trans |
| 4-w | OH | —(CH₂)₃—N(benzimidazol-2(3H)-one-N'-methyl) | trans |

TABLE I-2-continued
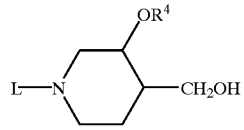
| Interm. No. | OR⁴ | L | physical data |
|---|---|---|---|
| 4-x | OH | 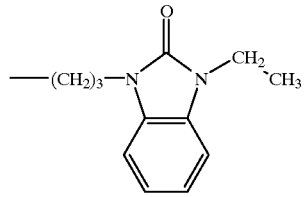 —(CH₂)₃—N(C=O)N(CH₂CH₃)— benzimidazolone | >260° C., trans.HCl |
| 4-y | OH | —(CH₂)₃—N(C=O)N(CH₂CH₃)— benzimidazolone | cis |
| 4-z | OH | —(CH₂)₃—N(C=O)N(CH₂CH₃)— benzimidazolone | >260° C., cis.HCl |
| 4-aa | OH | 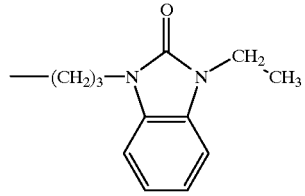 —(CH₂)₂—N(C=O)N—CH(CH₃)₂ imidazolone | trans |
| 4-bb | OH | 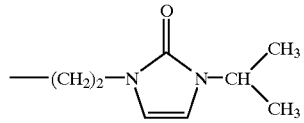 —(CH₂)₂—N—N=, 6-chloropyridazinone | trans |
| 4-cc | OH | —CH₂—CH=CH—C₆H₄—F | E-trans |
| 4-dd | OH | 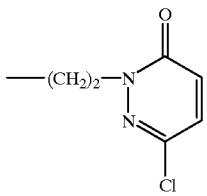 —(CH₂)₂—N—N=, 6-chloropyridazinone | cis |

TABLE I-2-continued

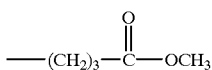

| Interm. No. | OR⁴ | L | physical data |
|---|---|---|---|
| 4-ee | OH | —(CH₂)₃—C(=O)—OCH₃ | cis |

EXAMPLE I-5

A mixture of (±)-cis-1-(2-aminoethyl)-3-hydroxy-4-piperidinemethanol (0.064 mol), 2-chloro-3-methylpyrazine (0.068 mol) and calcium oxide (0.145 mol) was stirred for 5 hours at 120° C. The reaction mixture was cooled. The mixture was dissolved in $CH_2Cl_2/CH_3OH$ and filtered over dicalite. The filtrate was evaporated and the residue was purified by column chromatography over silica gel (eluent: $CH_2Cl_2/(CH_3OH/NH_3)$ 90/10). The desired fractions were collected and the solvent was evaporated. The oily residue was triturated in $CH_3CN$. The precipitate was filtered off and dried, yielding 4 g (23.5%) of (±)-cis-1-[2-[(3-methyl-2-pyrazinyl)amino]ethyl]-3-hydroxy-4-piperidinemethanol (interm. 5a).

In a similar manner were also prepared:

TABLE I-3

| Interm. No. | OR⁴ | L | physical data |
|---|---|---|---|
| 5-a | OH | —(CH₂)₂—NH—(3-methylpyrazin-2-yl) | cis |
| 5-b | OCH₃ | —(CH₂)₂—NH—(3-methylpyrazin-2-yl) | cis |
| 5-c | OH | —(CH₂)₂—NH—(3-methylpyrazin-2-yl) | trans |
| 5-d | OH | —(CH₂)₃—NH—(3-cyanopyridin-2-yl) | trans |
| 5-e | OH | —(CH₂)₄—NH—(3-cyanopyridin-2-yl) | trans |
| 5-f | OH | —(CH₂)₃—NH—(3-cyanopyridin-2-yl) | cis |
| 5-g | OH | —(CH₂)₄—NH—(3-cyanopyridin-2-yl) | cis |
| 5-h | OH | 4-methylpiperidin-1-yl-(3-methylpyrazin-2-yl) | trans |
| 5-i | OH | —(CH₂)₃—NH—C(=O)—phenyl | trans |

EXAMPLE I-6

A mixture of (±)-1,1-dimethylethyl cis-4-[[(4-amino-5-chloro-2-methoxybenzoyl)oxy]-methyl]-3-hydroxy-1- piperidinecarboxylate (0.053 mol) in THF (250 ml) and a mixture of HCl and 2-propanol (25 ml) was stirred for 2 hours at room temperature, then for 10 minutes at 50° C., then cooled again to room temperature. The mixture was alkalinized with $NH_3$. The organic layer was separated, dried ($MgSO_4$), filtered and the solvent was evaporated. The residue was purified by column chromatography over silica gel (eluent: $CH_2Cl_2/(CH_3OH/NH_3)$ 90/10). The pure fractions were collected and the solvent was evaporated, yielding 4.6 g (29%) (±) cis-(3-hydroxy-4-piperidinyl)methyl 4-amino-5-chloro-2-methoxybenzoate (interm. 6-a).

In a similar manner were also prepared:

TABLE I-4

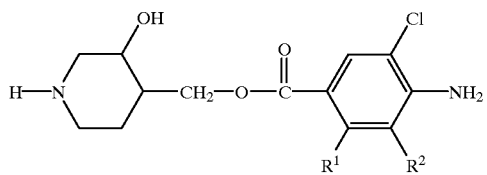

| Interm. No. | $OR^4$ | $R^1$ | $R^2$ | physical data |
|---|---|---|---|---|
| 6-b | $OCH_3$ | —$CH_3O$ | —H | cis |
| 6-c | $OCH_3$ | —O—C($CH_3$)$_2$—$CH_2$— | | cis |
| 6-d | OH | —O—($CH_2$)$_2$—O— | | trans |
| 6-e | OH | —O—C($CH_2$)$_2$—$CH_2$— | | cis |
| 6-f | OH | —O—($CH_2$)$_3$—O— | | trans |
| 6-g | OH | —O—$CH_2$—O— | | trans |
| 6-h | OH | —O—($CH_2$)$_3$—O— | | cis |
| 6-i | OH | —O—($CH_2$)$_2$—O— | | cis |
| 6-j | OH | —$OCH_3$ | —$OCH_3$ | 169–170° C. trans |
| 6-k | OH | —O—$CH_2$—O— | | 185–186° C. cis |
| 6-l | OH | —O—($CH_2$)$_2$— | | >280° C. trans |
| 6-m | OH | —O—C($CH_3$)$_2$—$CH_2$— | | 197–198° C. trans.HCl |
| 6-n | OH | —O—C($CH_3$)$_2$—$CH_2$— | | trans |

EXAMPLE I-7

NaH (60% oily dispersion) (0.05 mol) was added under $N_2$ atmosphere to a mixture of (±)-trans-3-hydroxy-4-piperidinemethanol (0.053 mol) and 1H-imidazole (0.12 mol) in THF (150 ml). The mixture was stirred for 5 min at room temperature. 1-(4-amino-5-chloro-2-methoxybenzoyl)-1H-imidazole (0.023 mol) was added at room temperature and the resulting reaction mixture was stirred for 5 min at room temperature. The solvent was evaporated. The residue was diluted with water and extracted twice with $CH_2Cl_2$. The organic layer was separated, dried ($MgSO_4$), filtered and the solvent was evaporated. The residue was crystallized from $CH_3CN$. The precipitate was filtered off and dried, yielding 1.69 g of intermediate 7-a (see table). This fraction was recrystallized from methanol. The precipitate was filtered off and dried yielding 0.83 of intermediate 7-a (11.5%) (mp 160° C.)

In this manner and in a similar manner were prepared:

TABLE I-5

| Interm. No. | $OR^4$ | $R^1$ | $R^2$ | physical data |
|---|---|---|---|---|
| 7-a | OH | —O—($CH_2$)$_2$— | | cis |
| 7-b | OH | —$OCH_3$ | —H | 159–160° C. trans |
| 7-c | OH | —$OCH_3$ | —$OCH_3$ | cis, ½ $C_2H_2O_4$(*) 227–228° C. |
| 7-d | OH | —$OCH_3$ | —$OCH_3$ | cis. |
| 7-e | OH | —O—C($CH_3$)$_2$—$CH_2$— | | cis |
| 7-f | OH | —O—$CH_2$—O— | | trans |

(*)½ $C_2H_2O_4$ indicates a ethanedioic acid salt (2:1)

EXAMPLE I-8 a) $CaCO_3$ (32.5 g) was added to a mixture of 3,4-dihydro-2H-1,5-benzodioxepin-6-amine (J. Med. Chem. (1988), 31 (10)), 1934) (0.25 mol) in $CH_2Cl_2$ (400 ml) and $CH_3OH$ (200 ml). This mixture was stirred at room temperature. N,N,N-trimethylbenzenemethanaminium dichloroiodate (0.25 mol) was added portionwise at room temperature. The resulting reaction mixture was stirred for 30 min at room temperature. The mixture was diluted with water. The layers were separated. The aqueous phase was extracted with $CH_2Cl_2$. The combined organic layers were washed with water, dried ($MgSO_4$), filtered and the solvent evaporated. The residue was purified by column chromatography over silica gel (eluent: $CH_2Cl_2$). Two pure fractions were collected and the solvent was evaporated. The first residue (7 g) was crystallized from petroleum benzin. The precipitate was filtered off and dried, yielding: 5.26 g (1). The second residue (45 g) was crystallized from petroleum benzin. The precipitate was filtered off and dried, yielding: 40.5 g (2). Total yield: 45.76 g or 62.9% of 3,4-dihydro-9-iodo-2H-1,5-benzodioxepin-6-amine.(intermed 8-a).

b) Acetic acid anhydride (0.13 mol) was added dropwise to a mixture of intermediate 8a (0.127 mol) in HOAc (450 ml), stirred at room temperature. The reaction mixture was stirred for 30 min at room temperature. The reaction mixture was poured out into water (500 ml). The precipitate was filtered, washed with water, then dried, yielding: 39.2 g or 92.7% of N-[3,4-dihydro-9-iodo-2H-1,5-benzdiazepin-6-yl] acetamide (intermed. 8-b).

c) A mixture of intermediate 8-b (0.116 mol), KOAc (20 g) and palladium on carbon (10%) (2 g, as a catalyst) in $CH_3OH$ (500 ml) was stirred at 150° C. under 4.9 $10^6$ Pa pressure of CO, during 16 hours. The reaction mixture was cooled, filtered over dicalite, and the filtrate was evaporated. The residue was diluted with water, then extracted twice with $CH_2Cl_2$. The combined organic layers were dried ($MgSO_4$), filtered and the solvent evaporated. The residue was dissolved in acetic acid and acetic acid anhydride (5 ml) was added. The mixture was stirred for 10 min at room temperature, then diluted with water and extracted twice with $CH_2Cl_2$. The separated organic phase was washed with water, with NaOH (10% aqueous solution), again with water, then dried (MgSO$_4$), filtered and the filtrate was evaporated. The residue was suspended in DIPE, filtered off and dried, yielding: 24 g or 78.1% of methyl 3,4-dihydro-9-acetylamino-2H-1,5-benzodiazepine-6-carboxylate. (intermed 8-c).

d) A mixture of intermediate 8-c (0.10 mol) and N-bromosuccinimide (0.11 mol) in (CH$_3$CN (250 ml) was stirred and refluxed for one hour. The reaction mixture was cooled, and poured out into water. This mixture was extracted twice with CH$_2$Cl$_2$. The separated organic layer was washed with water, dried (MgSO$_4$), filtered and the solvent evaporated. The residue was suspended in DIPE, filtered off and dried, yielding 27.38 g (91.3%) of methyl 8-chloro-3,4-dihydro-9-acetylamino-2H-1,5-benzodiazepine-6-carboxylate (intermed. 8-d).

e) Intermediate 8-d (0.091 mol) was added to KOH (0.91 mol) in H$_2$O (500 ml) and the resulting reaction mixture was stirred and refluxed for 3 hours. The reaction mixture was cooled and acidified with HCl (36% aqueous solution) (pH=±4). The precipitate was filtered off, washed with water, then dried, yielding: 21.53 g (97.1%) of 8-chloro-3,4-dihydro-9-acetylamino-2H-1,5-benzodiazepine-6-carboxylic acid (intermed 8-e).

EXAMPLE I-9 a) A mixture of N-(2,3-dimethoxyphenyl)-acetamide (Eur.J.Med.Chem. (1988), 23, 6, pp 501–510) (0.91 mol) and N-bromosuccinimide (0.91 mol) in CH$_3$CN (2000 ml) was stirred and refluxed for 1 hour. The mixture was cooled, poured out into H$_2$O (2000 ml) and extracted twice with CH$_2$Cl$_2$. The combined organic layers were washed with H$_2$O, dried (MgSO$_4$), filtered and the solvent was evaporated. The residue was crystallized from DIPE. The precipitate was filtered off and dried. Yielding: 93.8 g N-(6-chloro-2,3-dimethoxyphenyl)-acetamide (44.9%) (intermed 9-a).

b) A solution of intermediate 9-a (0.59 mol) in HCl (20% aqueous solution) (1500 ml) was stirred and refluxed for 2 hours. The mixture was cooled, alkalinized with NaOH (50% aqueous solution) and extracted twice with CH$_2$Cl$_2$. The combined organic layers were washed with water, dried (MgSO$_4$), filtered, and the solvent was evaporated, yielding 110 g (100%) of 6-chloro-2,3-dimethoxybenzenamine (intermed 9-b).

c) A mixture of intermediate 9-b (0.59 mol) and CaCO$_3$ (75 g) in CH$_2$Cl$_2$ (600 ml) and CH$_3$OH (300 ml) was stirred at room temperature. N,N,N-trimethylbenzenemetanaminium dichloroiodate (0.6 mol) was added portionwise and the mixture was stirred and refluxed for 1 hour. The mixture was cooled and diluted with H$_2$O (1.5 l). The organic layer was separated and the aqueous layer was extracted again with CH$_2$Cl$_2$. The combined organic layers were washed with H$_2$O, dried (MgSO$_4$), filtered, and the solvent was evaporated. The residue (170 g) was purified by column chromatography over silica gel (eluent: CH$_3$OH/H$_2$O 80/20). The desired fractions were collected and the solvent was evaporated, yielding: 114.16 g (61.7%) of 6-chloro-4-iodo-2,3-dimethoxybenzenamine(intermed 8-c).

d) A mixture of intermed 8-c (0.36 mol), potassium acetate (45 g) and palladium on carbon (10%) (2 g) in CH$_3$OH (450 ml) was stirred at 125° C. under CO (4.9 10$^6$ Pa CO pressure) for 18 hours. The mixture was cooled and filtered over hyflow. The filtrate was evaporated. The residue was diluted with H$_2$O and extracted three times with CH$_2$Cl$_2$. The combined organic layers were dried (MgSO$_4$), filtered, and the solvent was evaporated. The residue was purified by column chromatography over silica gel (eluent: CH$_2$Cl$_2$). The desired fractions were collected and the solvent was evaporated, yielding: 67.1 g (75.9%) of 4-amino-5-chloro-2,3-dimethoxy-benzoate methyl ester (intermediate 8-d).

e) A mixture of intermed 8-d (0.27 mol) and KOH (2.7 mol) in H$_2$O (1000 ml) was stirred and refluxed for 2 hours. The reaction mixture was cooled and acidified with HCl (36%), and the resulting precipitate was filtered off, washed with water and dried, yielding: 53 g (84.8%) 4-amino-5-chloro-2,3-dimethoxy-benzoic acid (intermed 8-e).

EXAMPLE I-10

A mixture of 4-amino-5-chloro-2,3-dihydro-2,2-dimethyl-7-benzofurancarboxylic acid (0.3 mol) and 1,1'-carbonyldiimidazole (0.3 mol) in CH$_3$CN (1000 ml) was stirred for 1.5 hours at room temperature. The solvent was evaporated. The residue was partitioned between water and CH$_2$Cl$_2$. The organic layer was separated, dried (MgSO$_4$), filtered and the solvent evaporated. The residue was suspended in DIPE, filtered off and dried (vacuum, 50° C.), yielding 50 g (58%) of N-[4-amino-5-chloro-2,3-dihydro-2,2-dimethyl-7-benzofurancarboyl] 1H-imidazole (intermediate 9-a).

In a similar manner were also prepared:

N-[4-amino-5-chloro-2,3-dihydro-7-benzofuranoyl]-1H-imidazole (intermed 9-b)

N-[8-chloro-3,4-dihydro-9-acetylamino-2H-1,5-benzdiazepine-6-oyl]-1H-imidazole (intermed 9-c)

N-[4-amino-5-chloro-2,3-dimethoxybenzoyl]-1H-imidazole (intermed 9-d).

Preparation of the Final Compounds

EXAMPLE F-1

Reaction under N$_2$ flow. Sodium hydride (60% oily dispersion) (0.013 mol) was added to a solution of (±)-trans-1-butyl-3-hydroxy-4-piperidinemethanol (0.013 mol) in THF (80 ml). The mixture was stirred and refluxed for 3 hours, then cooled (solution I). 8-amino-7-chloro-2,3-dihydro-1,4-benzodioxin-5-carboxylic acid (0.013 mol) was dissolved in acetonitrile (80 ml). 1,1'-Carbonylbis-1H-imidazole (0.015 mol) was added. The resulting mixture was stirred for 2 hours at room temperature. The solvent was evaporated. The residue was dissolved in THF (80 ml) (=solution II). Solution (II) was poured out into solution (I) and the resulting reaction mixture was stirred for 20 hours at room temperature. The solvent was evaporated. The residue was partitioned between water and CH$_2$Cl$_2$. The organic layer was separated, dried (MgSO$_4$), filtered and the solvent was evaporated. The residue was purified by column chromatography over silica gel (eluent: CH$_2$Cl$_2$/CH$_3$OH 93/7). The desired fractions were collected and the solvent was evaporated. The residue was dissolved in 2-propanol and converted into the ethanedioic acid salt (1:1). The mixture was cooled to 0° C. and the resulting precipitate was filtered off and dried (vacuum, 60° C.), yielding 1.5 g (24%) of (±)-trans-(1-butyl-3-hydroxy-4-piperidinyl)methyl 8-amino-7-chloro-2,3-dihydro-1,4-benzodioxin-5-carboxylate ethanedioate (1:1); mp. 201.6° C. (comp. 30).

EXAMPLE F-2

A mixture of (±)-cis-(3-hydroxy-4-piperidinyl)methyl 4-amino-5-chloro-2-methoxy benzoate (0.016 mol), bromobutane (0.02 mol) and N,N-diethylethanamine (0.03 mol)

in N,N-dimethylformamide (80 ml) was stirred for 20 hours at 60° C. The reaction mixture was cooled and the solvent was evaporated. The residue was purified by column chromatography over silica gel (eluent: $CH_2Cl_2/CH_3OH$ 90/10). The pure fractions were collected and the solvent was evaporated. The residue was repurified by column chromatography over silica gel (eluent: $CH_2Cl_2/(CH_3OH/NH_3)$ 95/5). The pure fractions were collected and the solvent was evaporated. The residue was crystallized from $CH_3CN$. The resulting precipitate was filtered off and dried (vacuum; 50° C.), yielding 1.4 g (24%) of (±)-cis-(1-butyl-3-hydroxy-4-piperidinyl)methyl 4-amino-5-chloro-2-methoxybenzoate; mp. 121.4° C. (comp. 3).

EXAMPLE F-3

(±)-trans-(1-butyl-3-hydroxy-4-piperidinyl)methyl 8-amino-7-chloro-2,3-dihydro-1,4-benzodioxin-5-carboxylate ethanedioate(1:1) (0.0055 mol) was prepurified by reversed-phase column chromatography over RP-18 (eluent: (0.5% $NH_4OAc$ in $H_2O$)/$CH_3OH$ 35/65), then separated into its optical isomers (resolution) by chiral column chromatography over Chiralcel OD (eluent: hexane/ethanol 85/15). Two desired fraction groups were collected and their solvent was evaporated. Each residue was (separately) purified by column chromatography over silica gel (eluent: $CH_2Cl_2/CH_3OH$ 94/6). The pure fractions of each enantiomer were collected and the solvent was evaporated, giving 0.540 g of the (−)-enantiomer and 0.330 g of the (+)-enantiomer. The oil comprising the (−)enantiomer was suspended in DIPE, filtered off, then dried (vacuum, 40° C.), yielding 0.49 g of ((−)-trans)-(1-butyl-3-hydroxy-4-piperidinyl)methyl 8-amino-7-chloro-2,3-dihydro-1,4-benzodioxin-5-carboxylate (comp. 32); $[a]_D^{20}$=−31.12 (conc.=4.89 mg/5ml in $CH_3OH$). The oil comprising the (+)-enantiomer was suspended in DIPE, filtered off, then dried (vacuum, 40° C.), yielding 0.3 g ((+)-trans)-(1-butyl-3-hydroxy-4-piperidinyl)methyl 8-amino-7-chloro-2,3-dihydro-1,4-benzodioxin-5-carboxylate (comp. 33); $[a]_D^{20}$=+31.31 (conc.=5.27 mg/5 ml in $CH_3OH$).

EXAMPLE F-4

A mixture of compound 37 (see table 1)(0.0052 mol) and HCl (5 ml) in THF (52 ml) was stirred and refluxed for one hour. The reaction mixture was cooled, alkalinized with $NH_3$, and the solvent was evaporated. The residue was partitioned between $NH_3$/water and $CH_2Cl_2$. The organic layer was separated, dried ($MgSO_4$), filtered and the solvent was evaporated. The residue was triturated in DIPE, filtered off, then crystallized from $CH_3CN$. The precipitate was filtered off and dried, yielding 0.75 g (37.5%) of compound 38 (see table 1).

EXAMPLE F-5

Intermediate 6-d (0.007 mol) was dissolved in $CH_3OH$ (70 ml). Oxirane (gas) was allowed to bubble through the solution during 2 hours. The solvent was evaporated. The residue was purified by column chromatography over silica gel (eluent: $CH_2Cl_2/CH_3OH$ 90/10). The pure fractions were collected and the solvent was evaporated. The residue was crystallized from $CH_3CN$ (0° C.). The precipitate was filtered off and dried (vacuum; 50° C.), yielding 0.85 g (32%) of compound 78 (see table 5).

EXAMPLE F-6

A mixture of intermediate 6-d (0.01 mol) and ethanal (0.01 mol; solution in THF) in THF (150 ml) was hydrogenated with platinum on carbon (1 g) as a catalyst in the presence of thiophene (4% solution, 1 ml). After uptake of $H_2$ (1 equiv.), the catalyst was filtered off and the filtrate was evaporated. The residue was purified by column chromatography over silica gel (eluent: $CH_2Cl_2/(CH_3OH/NH_3)$ 95/5). The pure fractions were collected and the solvent was evaporated. The residue was crystallized from DIPE with a small amount of $CH_3CN$. The precipitate was filtered off and dried (vacuum, 40° C.), yielding 1 g (27%) of compound 79 (see table 5).

EXAMPLE F-7

In an autoclave (CO-pressure=50 kg), a mixture of intermediate 4-m (0.019 mol), 6-chlor-2,3-dihydro-8-iodo-1,4-benzodioxin-5-amine (0.013 mol), palladium on carbon (1 g) and N,N-diethylethanamine (4 g) in $CH_3CN$ (100 ml) was heated for 20 hours at 100° C. The reaction mixture was cooled, filtered and the filtrate was evaporated. The residue was partitioned between water and $CH_2Cl_2$. The organic layer was separated, dried ($MgSO_4$), filtered and the solvent was evaporated. The residue was purified by column chromatography over silica gel (eluent: $CH_2Cl_2/(CH_3OH/NH_3)$ 95/5). The desired fractions were collected and the solvent was evaporated. The residue was dissolved in 2-propanol and converted into the ethanedioic acid salt (1:1). The precipitate was filtered off and dried (vacuum, 40° C.), yielding 2.5 g (33%) of compound 108 (see table 5). This fraction was repurified by column chromatography over silica gel. (eluent: $CH2Cl_2/CH_3OH$ 95/5). The pure fractions were collected and the solvent was evaporated. The residue was solidified and crystallized as an ethanedioic acid salt in 2-propanol. The precipitate was filtered off and dried. Yielding: 1 g compound 108 (see table 5).

EXAMPLE F-8

Compound 32 (0.0025 mol) was stirred in 2-propanol (20 ml) for 15 min at room temperature. The resulting suspension was heated until complete dissolution (nearly at reflux temperature). The mixture was cooled to room temperature. HCl in 2-propanol (18 drops) was added dropwise over a 15-min period and slowly precipitation resulted. The reaction mixture was stirred for one hour at room temperature. The precipitate was filtered off, washed with 2-propanol (5 ml), then dried (vacuum, 40° C.). The filtrate was treated with HCl in 2-propanol (21 drops) and 2-propanol (30 ml), and the above reaction procedure was repeated. A total yielding of 1.5 g compound 109 (see table 5).

TABLE F-1

[Structure: piperidine with OR⁴ at position 3, CH₂-O-C(=O)- linked to benzene ring bearing OCH₃, NH₂, and Cl substituents; N-substituted with L]

| Co. No. | Ex. No. | —L | OR⁴ | physical data mp. in ° C. |
|---|---|---|---|---|
| 1 | F-2 | —(CH₂)₃—CH₃ | OCH₃ | 107.9° C.; cis |
| 2 | F-2 | —(CH₂)₂—O—(CH₂)₂—OH | OCH₃ | 130.4° C.; cis |
| 3 | F-2 | —(CH₂)₃—CH₃ | OH | 121.4° C.; cis |
| 4 | F-2 | —CH₂—CH₃ | OCH₃ | 98.9° C.; cis |
| 5 | F-1 | —(CH₂)₃—O-(4-fluorophenyl) | OCH₃ | 72.5° C.; cis |
| 6 | F-1 | —(CH₂)₂—NH-(3-methyl-2-pyrazinyl) | OH | 158.4° C.; cis |
| 7 | F-1 | —(CH₂)₂—NH-(3-methyl-2-pyrazinyl) | OCH₃ | 172.2° C.; cis |
| 8 | F-1 | —(CH₂)₃—CH₃ | OH | 95.3° C.; trans |
| 9 | F-1 | —(CH₂)₂—NH-(3-methyl-2-pyrazinyl) | OH | 80–90° C.; trans |
| 34 | F-1 | —(CH₂)₃—CN | OH | 129–130° C.; trans |
| 35 | F-1 | —(CH₂)₃—O—CH₃ | OH | 117–118° C.; cis |
| 36 | F-1 | —(CH₂)₃—O-(4-fluorophenyl) | OH | 164–165° C.; trans |
| 37 | F-1 | —(CH₂)₃—C(CH₃)(OCH₂CH₂O) [2-methyl-1,3-dioxolan-2-yl] | OH | 119–120° C.; cis |
| 38 | F-4 | —(CH₂)₃—C(=O)—CH₃ | OH | 118–119° C., cis |
| 39 | F-1 | —CH₂-2-tetrahydrofuranyl | OH | 168–169° C.; trans |
| 40 | F-1 | —(CH₂)₃—(6-methyl-3-oxo-2,3-dihydropyridazin-2-yl) | OH | 140° C.; trans |

TABLE F-2

[Structure: piperidine with OR⁴ at position 3, CH₂-O-C(=O)- linked to a 2,3-dihydrobenzofuran ring bearing NH₂ and Cl substituents; N-substituted with L]

| Co. No. | Ex. No. | —L | OR⁴ | physical data mp.° C. |
|---|---|---|---|---|
| 10 | F-1 | —(CH₂)₃—CH₃ | OH | 152.6° C.; cis |
| 11 | F-1 | —(CH₂)₃—CH₃ | OCH₃ | 112.4° C.; cis |
| 12 | F-1 | —CH₂—CH₃ | OCH₃ | 145.1° C.; cis |
| 13 | F-1 | —(CH₂)₃—O-(4-fluorophenyl) | OCH₃ | 168.4° C.; cis |
| 14 | F-1 | —CH₂—(2-tetrahydrofuranyl) | OCH₃ | 144.6° C.;.(COOH)₂; cis |
| 15 | F-1 | —(CH₂)₂—NH-(3-methyl-2-pyrazinyl) | OCH₃ | 195.0° C.; cis |
| 16 | F-1 | —(CH₂)₃—CH₃ | OH | 82.1° C.; trans |
| 41 | F-1 | —CH₂-(2-tetrahydrofuranyl) | OH | cis |

TABLE F-2-continued
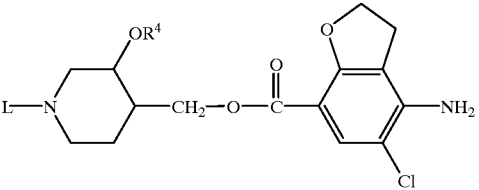
| Co. No. | Ex. No. | —L | OR⁴ | physical data mp.° C. |
|---|---|---|---|---|
| 42 | F-1 | 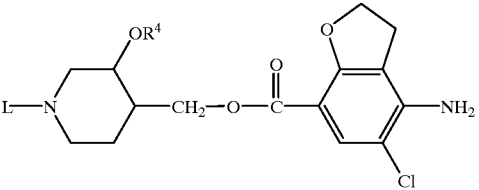 | OH | cis |
| 43 | F-1 | 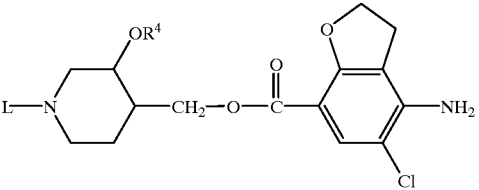 | OH | cis |
| 44 | F-4 | 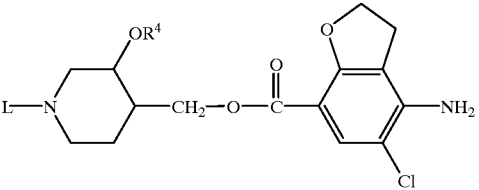 | OH | 124° C.; cis |
| 45 | F-1 | 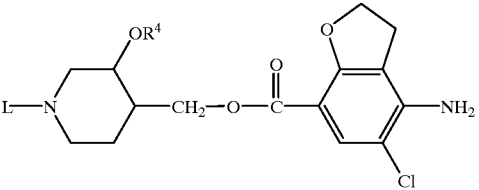 | OH | ±117° C.; cis |
| 46 | F-1 | 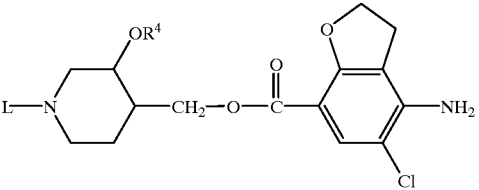 | OH | 148° C.; cis |
| 47 | F-1 | 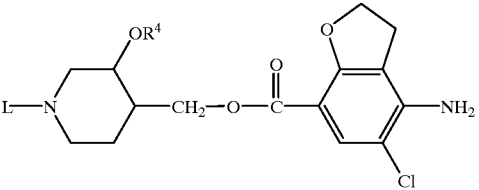 | OH | 152° C.; cis |
| 48 | F-1 | 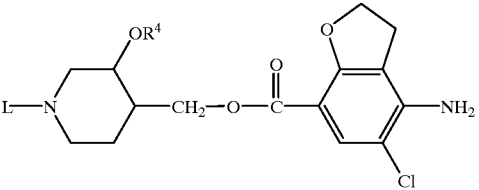 | OH | cis |
| 49 | F-1 | —(CH$_2$)$_3$—O—CH$_3$ | OH | 98° C.; trans |
| 50 | F-1 | —CH$_2$-(2-tetrahydrofuranyl) | OH | 136–137° C.; trans |
| 51 | F-1 | 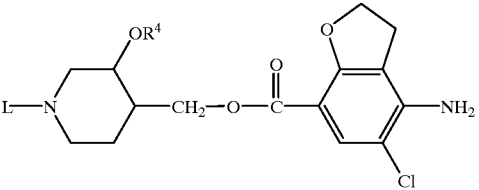 | OH | 110° C.; trans |
| 52 | F-4 | 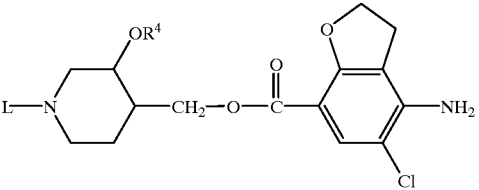 | OH | 103° C.; trans |
| 53 | F-1 | —(CH$_2$)$_3$—O—CH$_3$ | OH | 139° C., cis |

TABLE F-2-continued

Structure: Piperidine with OR⁴ group at 3-position and L at N, with CH₂-O-C(=O) linker to 2,3-dihydrobenzofuran bearing NH₂ and Cl substituents.

| Co. No. | Ex. No. | —L | OR⁴ | physical data mp.° C. |
|---|---|---|---|---|
| 54 | F-1 | —(CH₂)₂—N(C(=O)CH=CHC(CH₃)=N—) (6-methyl-3(2H)-pyridazinone-2-yl) | OH | 139–140° C., cis |
| 55 | F-1 | —(CH₂)₂—N (phthalazin-1(2H)-one-2-yl) | OH | 109–110° C., cis |
| 56 | F-2 | —(CH₂)₂—O—(CH₂)₂—OH | OH | 123–124° C., trans |
| 57 | F-1 | —(CH₂)₃—CN | OH | 135–136° C., cis |
| 58 | F-1 | —(CH₂)₃—CN | OH | 114–115° C., trans |
| 59 | F-2 | —(CH₂)₂—O—(CH₂)₂—OH | OH | 99–100° C., cis |
| 60 | F-1 | —(CH₂)₃—C(=O)—N(pyrrolidinyl) | OH | ±190° C.; trans |
| 61 | F-1 | —(CH₂)₃—N(benzimidazolin-2-one, N'-CH₂CH₃) | OH | 160–165° C., trans |
| 62 | F-1 | —(CH₂)₂—N(imidazolin-2-one, N'-CH(CH₃)₂) | OH | trans |
| 63 | F-1 | —(CH₂)₃—C(=O)—OCH₃ | OH | 75–78° C., cis |
| 64 | F-1 | —(CH₂)₂—N (6-chloro-3(2H)-pyridazinone-2-yl) | OH | decomposition; trans |

TABLE F-3

[Structure: piperidine with OR⁴ group, L-N, CH₂-O-C(=O)- linked to 2,2-dimethyl-2,3-dihydrobenzofuran bearing NH₂ and Cl substituents]

| Co. No. | Ex. No. | —L | OR⁴ | physical data mp. ° C. |
|---|---|---|---|---|
| 17 | F-2 | —CH₂—CH₃ | OCH₃ | 61.0° C.; cis; ½ H₂O |
| 18 | F-1 | —(CH₂)₃—CH₃ | OH | 140.1° C.; cis |
| 19 | F-1 | —(CH₂)₃—CH₃ | OCH₃ | 102.1° C.; cis |
| 20 | F-1 | —(CH₂)₃—O-(4-fluorophenyl) | OCH₃ | 123.0° C.; cis |
| 21 | F-1 | —(CH₂)₃—CH₃ | OH | 77.2° C.; trans |
| 22 | F-1 | —(CH₂)₂—NH-(3-methyl-2-pyrazinyl) | OH | 194.4° C.; cis |
| 23 | F-1 | —(CH₂)₂—NH-(3-methyl-2-pyrazinyl) | OH | trans |
| 65 | F-2 | —CH₂—(2-tetrahydrofuranyl) | OH | cis |
| 66 | F-2 | —(CH₂)₃—[2-methyl-1,3-dioxolan-2-yl (CH₃)] | OH | cis |
| 184 | F-4 | —(CH₂)₃—C(=O)—CH₃ | OH | cis |
| 67 | F-1 | —(CH₂)₃—NH-(3-cyano-2-pyridinyl) | OH | ±139° C.; cis |
| 68 | F-1 | —(CH₂)₃—O—cyclohexyl | OH | cis |
| 69 | F-1 | —(CH₂)₄—NH-(3-cyano-2-pyridinyl) | OH | 138° C.; cis |
| 70 | F-1 | —(CH₂)₃—C(=O)—N(pyrrolidinyl) | OH | 158° C.; cis |
| 71 | F-1 | —(CH₂)₃—CN | OH | 162–163° C., trans |
| 72 | F-1 | —(CH₂)₃—O—CH₃ | OH | 117–118° C., trans |
| 73 | F-1 | —(CH₂)₂—(6-methyl-3-oxo-2,3-dihydropyridazin-2-yl) | OH | 199–200° C., trans |
| 74 | F-2 | —(CH₂)₂—O—(CH₂)₂—OH | OH | 99–100° C., trans |

TABLE F-3-continued
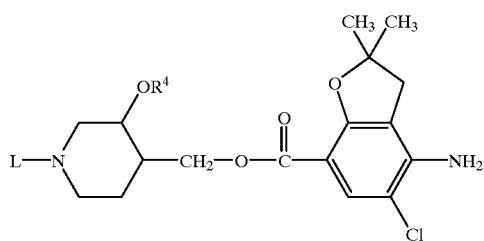
| Co. No. | Ex. No. | —L | OR⁴ | physical data mp. ° C. |
|---|---|---|---|---|
| 75 | F-1 |  | OH | 156° C., cis |
TABLE F-4
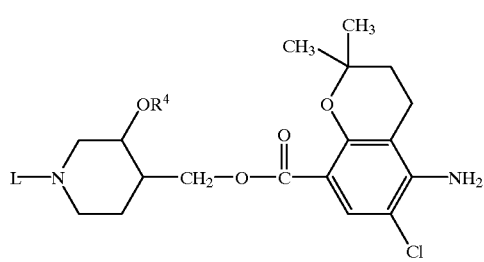
| Co. No. | Ex. No. | —L | OR⁴ | physical data mp. ° C. |
|---|---|---|---|---|
| 24 | F-1 | —(CH₂)₃—CH₃ | OCH₃ | 101.1° C.; cis |
| 25 | F-1 | —(CH₂)₃—CH₃ | OH | 185.1° C.; cis |
TABLE F-4-bis
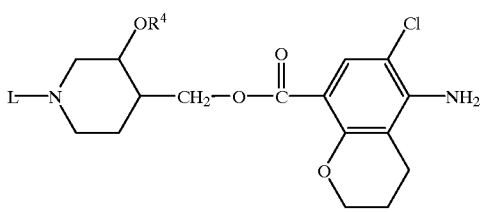
| Co. No. | Ex. No. | —L | OR⁴ | physical data mp. ° C. |
|---|---|---|---|---|
| 76 | F-1 |  | OH | 169–170° C., trans |
| 77 | F-4 | 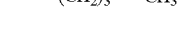 | OH | 199–200° C., trans |
TABLE F-5
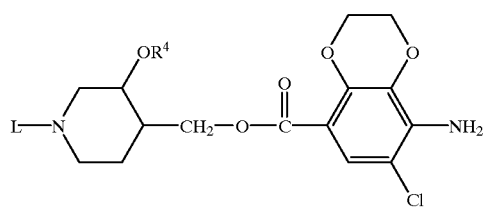

| Co. No. | Ex. No. | —L | OR⁴ | physical data mp. °C. |
|---|---|---|---|---|
| 26 | F-1 | —(CH$_2$)$_3$—CH$_3$ | OCH$_3$ | 197.8° C.; cis |
| 27 | F-1 | —(CH$_2$)$_3$—CH$_3$ | OH | 100° C.; cis |
| 28 | F-1 | —(CH$_2$)$_2$—NH-(3-methyl-2-pyrazinyl) | OH | 176.6° C.; cis |
| 29 | F-1 | —(CH$_2$)$_2$—NH-(3-methyl-2-pyrazinyl) | OCH$_3$ | 184.7° C.; cis |
| 30 | F-1 | —(CH$_2$)$_3$—CH$_3$ | OH | 201.6° C.; trans; |
| 31 | F-1 | —(CH$_2$)$_2$—NH-(3-methyl-2-pyrazinyl) | OH | trans |
| 32 | F-3 | —(CH$_2$)$_3$—CH$_3$ | OH | 106° C.; A-trans |
| 33 | F-3 | —(CH$_2$)$_3$—CH$_3$ | OH | 106° C.; B-trans |
| 78 | F-5 | —(CH$_2$)$_2$—OH | OH | trans |
| 79 | F-6 | —CH$_2$—CH$_3$ | OH | 130° C.; trans |
| 80 | F-2 | —(CH$_2$)$_3$—CN | OH | 168° C.; trans |
| 81 | F-6 | —(CH$_2$)$_5$—CH$_3$ | OH | 148° C.; trans |
| 82 | F-2 | —(CH$_2$)$_3$—O-(4-fluorophenyl) | OH | 158° C.; trans |
| 83 | F-1 | —(CH$_2$)$_3$—NH-(3-cyano-2-pyridinyl) | OH | 135° C.; trans |
| 84 | F-2 | —CH$_2$-(2-tetrahydrofuranyl) | OH | trans |
| 85 | F-2 | —(CH$_2$)$_2$-(7-methyl-5-oxo-2,3-dihydro-5H-thiazolo[3,2-a]pyrimidin-6-yl) | OH | ±142° C.; trans |
| 86 | F-2 | —(CH$_2$)$_2$—O—(CH$_2$)$_2$—OH | OH | 120° C.; trans |
| 87 | F-1 | —(CH$_2$)$_3$—O—CH(CH$_3$)$_2$ | OH | 180° C.; trans |
| 88 | F-2 | —(CH$_2$)$_3$-(2-methyl-1,3-dioxolan-2-yl) | OH | 170° C.; trans |
| 89 | F-2 | —(CH$_2$)$_2$-(2-tetrahydrofuranyl) | OH | ±130° C.; trans |
| 90 | F-5 | —(CH$_2$)$_3$—C(=O)—CH$_3$ | OH | 200° C.; trans |
| 91 | F-1 | —(CH$_2$)$_4$—NH-(3-cyano-2-pyridinyl) | OH | trans |
| 92 | F-2 | —(CH$_2$)$_3$-(6-chloro-3-oxo-2,3-dihydropyridazin-2-yl) | OH | ±138° C.; trans |
| 93 | F-1 | —(CH$_2$)$_3$—C(=O)—O—CH$_3$ | OH | 138° C.; trans |
| 94 | F-2 | —CH$_2$—CH=CH—CH$_3$ | OH | 98° C.; E-trans |
| 95 | F-1 | —CH$_2$-(2-tetrahydrofuranyl) | OH | ±119° C.; cis |

| 96 | F-2 | 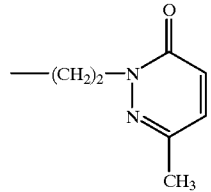 | OH | 170° C.; trans |
| --- | --- | --- | --- | --- |
| 97 | F-2 | 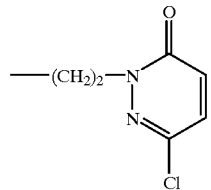 | OH | 140° C.; trans |
| 98 | F-1 | 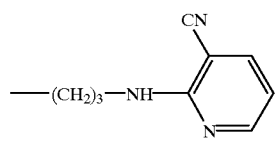 | OH | cis |
| 99 | F-1 | —(CH₂)₃—O—CH₃ | OH | trans |
| 100 | F-2 | 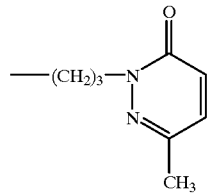 | OH | 160° C.; trans |
| 101 | F-1 | CH₂ cyclopropyl | OH | trans |
| 102 | F-1 | 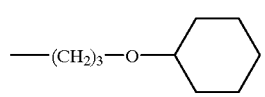 | OH | cis |
| 103 | F-1 | 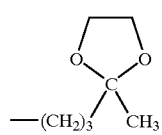 | OH | 112° C.; cis |
| 104 | F-2 | 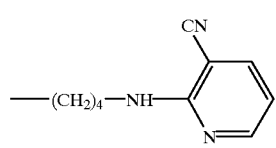 | OH | 116° C.; cis |
| 105 | F-5 | 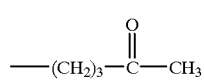 | OH | 75° C.; cis |
| 106 | F-2 | 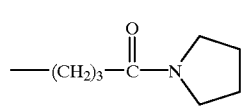 | OH | 176° C.; trans |
| 107 | F-1 | 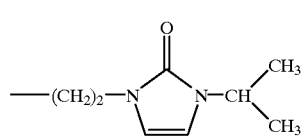 | OH | cis |
| 108 | F-7 | —(CH₂)₂—NH—SO₂—CH₃ | OH | trans |

| 109 | F-8 | —(CH$_2$)$_3$—CH$_3$ | OH | A-trans, HCl |
| 110 | F-8 | —(CH$_2$)$_3$—CH$_3$ | OH | A-trans, HBr |
| 111 | F-8 | —(CH$_2$)$_3$—CH$_3$ | OH | A-trans, fumarate |
| 112 | F-8 | —(CH$_2$)$_3$—CH$_3$ | OH | A-trans, nitrate |
| 113 | F-8 | —(CH$_2$)$_3$—CH$_3$ | OH | A-trans, malate (S) |
| 114 | F-8 | —(CH$_2$)$_3$—CH$_3$ | OH | A-trans, stearate |
| 115 | F-8 | —(CH$_2$)$_3$—CH$_3$ | OH | A-trans, phosphate |
| 116 | F-1 | —(CH$_2$)$_3$—O—CH$_3$ | OH | 117–118° C., cis |
| 117 | F-1 | 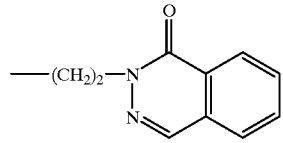 | OH | 169–170° C., trans |
| 118 | F-1 | 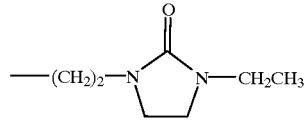 | OH | 189–190° C., trans |
| 119 | F-1 | 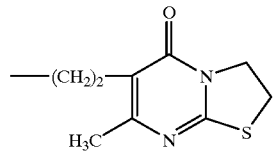 | OH | 169–170° C., cis |
| 120 | F-1 | —(CH$_2$)$_3$—CN | OH | 179–180° C., cis |
| 121 | F-1 | —(CH$_2$)$_3$—CH(4 fluorophenyl)$_2$ | OH | 149–150° C., trans |
| 122 | F-1 | 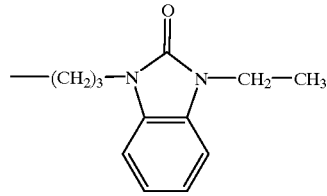 | OH | 147–148° C., trans |
| 123 | F-1 | 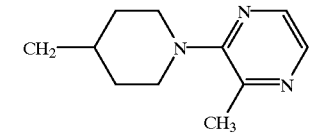 | OH | trans |
| 124 | F-1 | 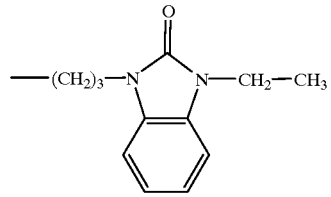 | OH | 165–167° C., cis |
| 125 | F-1 | 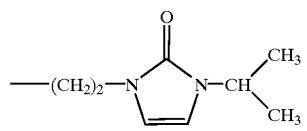 | OH | 200–201° C., trans |
| 126 | F-2 | —(CH$_2$)$_2$—O—(CH$_2$)$_2$—OH | OH | 180° C.; cis |
| 127 | F-1 | 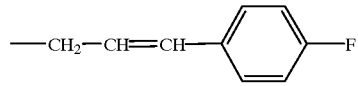 | OH | 151° C., E-trans |

| 128 | F-1 | 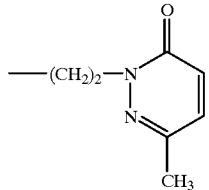 | OH | 180° C., cis |
|---|---|---|---|---|
| 129 | F-7 | 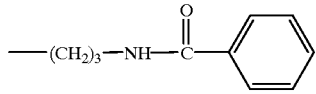 | OH | 141° C., trans |
| 130 | F-1 | 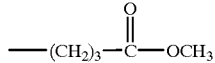 | OH | 163–164, cis |
TABLE F-6
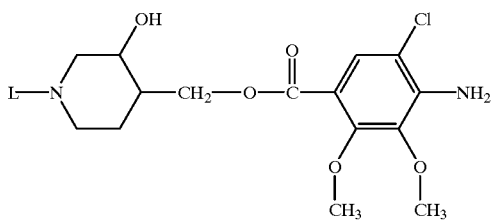
| Co. No. | Ex. No. | —L | OR⁴ | physical data mp. in ° C. |
|---|---|---|---|---|
| 131 | F-1 | —(CH₂)₃—CH₃ | OH | 110° C.; trans |
| 132 | F-8 | 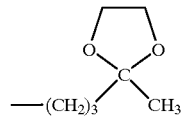 | OH | 148° C.; ½C₄H₄O₄.C₃H₈O(*), trans |
| 133 | F-1 | 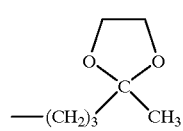 | OH | trans |
| 134 | F-4 | 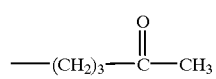 | OH | 190° C.; trans |
| 135 | F-1 | —(CH₂)₃—CH₃ | OH | 184° C.; cis |
| 136 | F-1 | 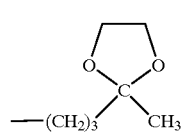 | OH | 158° C.; cis |
| 137 | F-4 | 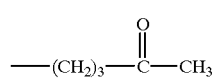 | OH | 170° C.; cis |
| 185 | F-1 | —CH₂-(2-tetrahydrofuranyl) | OH | cis |
| 138 | F-1 | —CH₂-(2-tetrahydrofuranyl) | OH | 193–194° C., trans |
| 139 | F-1 | 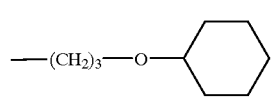 | OH | 160–161° C., cis |

TABLE F-6-continued
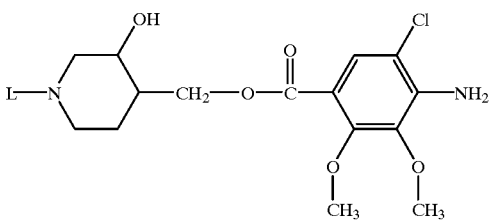
| Co. No. | Ex. No. | —L | OR⁴ | physical data mp. in ° C. |
|---|---|---|---|---|
| 140 | F-1 | 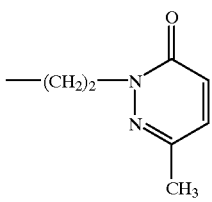 | OH | 150–151° C., trans |
| 141 | F-1 | 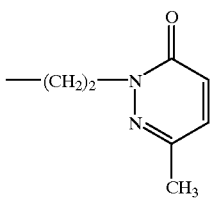 | OH | 127–128° C., cis |
| 142 | F-1 | 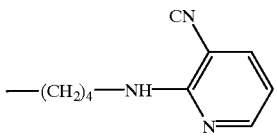 | OH | 153–154° C., cis |
| 143 | F-1 | —(CH$_2$)$_3$—O—CH$_3$ | OH | 179–180° C., trans |
| 144 | F-2 | —(CH$_2$)$_2$—O—(CH$_2$)$_2$—OH | OH | 136–137° C., cis |
| 145 | F-2 | —(CH$_2$)$_2$—O—(CH$_2$)$_2$—OH | OH | 159–160° C., trans |
| 146 | F-1 | 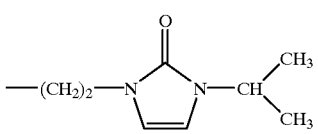 | OH | 130° C., cis |
| 147 | F-1 | 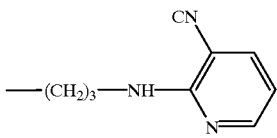 | OH | 105° C., cis |
| 148 | F-2 | 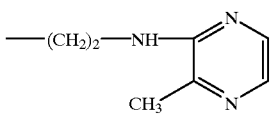 | OH | trans |
(*)½C$_4$H$_4$O$_4$.C$_3$H$_8$O means (E)-2-butenedioic acid salt (2:1).2-propanol TABLE F-7
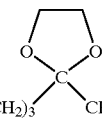
| Co. No. | Ex. No. | —L | OR$^4$ | physical data mp. in ° C. |
|---|---|---|---|---|
| 149 | F-1 | —(CH$_2$)$_3$—CH$_3$ | OH | 102° C.; trans |
| 150 | F-1 | 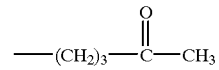 | OH | 118° C.; trans |
| 151 | F-4 | 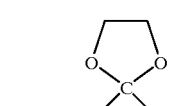 | OH | 148° C.; trans |
| 152 | F-1 | —(CH$_2$)$_3$—CH$_3$ | OH | 100° C.; cis |
| 153 | F-1 |  | OH | 119–120° C., cis |
| 154 | F-4 | 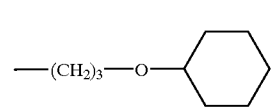 | OH | 97–98° C., cis |
| 155 | F-1 | —CH$_2$-(2-tetrahydrofuranyl) | OH | 119–120° C., cis |
| 156 | F-1 | —CH$_2$-(2-tetrahydrofuranyl) | OH | 205° C.; trans |
| 157 | F-1 | 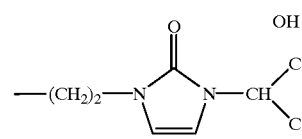 | OH | 89–90° C., cis |
| 158 | F-1 | —(CH$_2$)$_3$—O—CH$_3$ | OH | 152° C., cis |
| 159 | F-1 | —(CH$_2$)$_3$—CN | OH | 158° C., cis |
| 160 | F-1 | 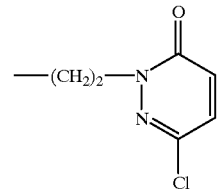 | OH | 164° C., cis |
| 161 | F-1 | 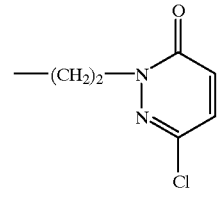 | OH | 190° C., trans |
| 162 | F-1 | 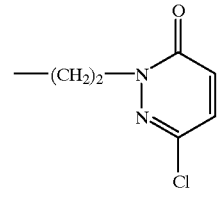 | OH | 200° C., cis |

TABLE F-7-continued

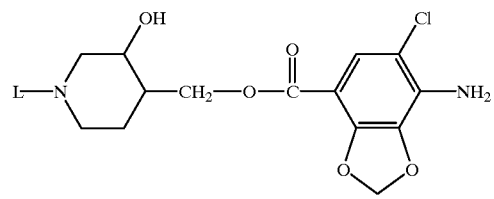

| Co. No. | Ex. No. | —L | OR⁴ | physical data mp. in ° C. |
|---|---|---|---|---|
| 163 | F-1 | —(CH₂)₃—O—CH₃ | OH | 176° C., trans |
| 164 | F-2 | —(CH₂)₂—O—(CH₂)₂—OH | OH | 126° C., trans |

TABLE F-8

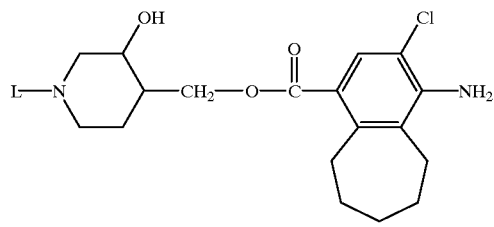

| Co. No. | Ex. No. | —L | OR⁴ | physical data mp. in ° C. |
|---|---|---|---|---|
| 165 | F-1 | —(CH₂)₃—CH₃ | OH | 153° C.; trans |
| 166 | F-1 | —(CH₂)₃—C(CH₃)(OCH₂CH₂O) (2-methyl-1,3-dioxolan-2-yl-propyl) | OH | trans |
| 167 | F-8 | —(CH₂)₃—C(CH₃)(OCH₂CH₂O) | OH | ½ C₄H₄O₄ (*), trans |
| 168 | F-4 | —(CH₂)₃—C(=O)—CH₃ | OH | 182° C.; trans |
| 169 | F-1 | —(CH₂)₃—CH₃ | OH | 98° C.; cis |
| 170 | F-1 | —CH₂-(2-tetrahydrofuranyl) | OH | 166° C.; trans |
| 171 | F-1 | —CH₂-(2-tetrahydrofuranyl) | OH | 137° C.; cis |
| 172 | F-8 | —(CH₂)₃—C(CH₃)(OCH₂CH₂O) | OH | C₂H₂O₄ (**), cis |
| 173 | F-4 | —(CH₂)₃—C(=O)—CH₃ | OH | 104° C.; cis |
| 174 | F-1 | —(CH₂)₃—C(CH₃)(OCH₂CH₂O) | OH | 166° C.; cis |

TABLE F-8-continued

[Structure: piperidine with OH at 3-position, N-L substituent, 4-position connected via CH₂-O-C(=O)- to benzene ring with Cl and NH₂ substituents, fused to a cycloheptane ring]

| Co. No. | Ex. No. | —L | OR⁴ | physical data mp. in ° C. |
|---|---|---|---|---|
| 175 | F-1 | —(CH₂)₃—O—cyclohexyl | OH | ±158° C.; cis |
| 176 | F-1 | —(CH₂)₄—NH—(3-CN-pyridin-2-yl) | OH | 134° C.; cis |
| 177 | F-1 | —(CH₂)₃—C(=O)—N-pyrrolidinyl | OH | 115–116° C., cis |
| 178 | F-1 | —(CH₂)₃—NH—(3-CN-pyridin-2-yl) | OH | 138° C., cis |
| 179 | F-1 | —(CH₂)₂—N(6-methyl-3-oxo-pyridazin-2-yl) | OH | 124–125° C., trans |
| 180 | F-1 | —(CH₂)₃—O—CH₃ | OH | 118–119° C., trans |
| 181 | F-1 | —(CH₂)₂—N(3-isopropyl-2-oxo-imidazol-1-yl) | OH | 191° C., cis |
| 182 | F-6 | —(CH₂)₂—OH | OH | 150° C., trans |
| 183 | F-1 | —(CH₂)₂—NH—(3-methyl-pyrazin-2-yl) | OH | trans |

(*)½ C₄H₄O₄ means (E)-2-butenedioic acid salt (2:1)
(**)C₂H₂O₄ means ethanedioic acid salt (1:1)

PHARMACOLOGICAL EXAMPLE P-1

Gastrointestinal Motility in Conscious Dog

Strain gauge force transducers were calibrated before implantation (Schuurkes et al., 1978). Female beagle dogs, weighing 7–17 kg, were implanted with isometric force transducers, under general anesthesia and aseptic precautions. After a median laparotomy, 4 transducers were sutured on the serosal side of either stomach and duodenum (to measure antroduodenal motility). To study motility of the stomach, the small intestines and the antroduodenal-coordination, transducers were placed on the antrum (4 cm distance of the pylorus), on the pylorus and the duodenum (4 and 8 cm distance of the pylorus). The wires were led via a subcutaneous tunnel on the left costal flank through a stab-wound between the scapulae. The connector was soldered to the lead wires and protected by a canvas jacket. Dogs were allowed a recovery period of at least two weeks. Experiments were started after a fasting period of ±20 hours, during which water was available ad libitum. During the experiments, dogs were free to move in their cages. The cages were built in a special room, provided with glass pervious to light in one direction, i.e. the observator can see the dogs while the dogs can not see the observator. Via this system it was possible to observe the dogs for behavioral changes and to determine defecation events. The information from the transducers was transmitted in digitized form (sampled at 5 Hz) by a small transmitter box. This box was placed in a jacket worn by the dog. The signals were received via a microphone above each cage and were transmitted to a central computer system (5 Hz rate). It is possible to monitor the motility of 8 dogs (4 channels per dog) 24 hours a day.

Dogs with strain gauge force transducers, were fed in the quiescent phase of the interdigestive state, 30 min after the passage of a migrating motor complex (MMC) (phase III). The meal consisted of 75 g dog feed.

Two hours after feeding, solvent or test compound was administered p.o. (in a volume ≦5 ml, preceded and followed by 2.5 ml water, via an orogastric tube). Antroduodenal motility was followed for at least 10 hours after drug administration.

The mean amplitude of the contractions of antrum, pylorus and duodenum during a period of 30 min was calculated as % of the mean maximal contractions during a migrating motor complex (MMC). Drug effects on the amplitude of contractions one hour after administration were expressed in percentage of the amplitude 30 min before administration of the drugs. These effects were compared with the effects after solvent administration on the same dogs in the same period.

Improvement of coordination was also evaluated.

TABLE P-1

Effect of compound 30 on antrum, pylorus, duodenum and coordination
ΔA means the mean amplitude increase of the contractions of the antrum (expressed in % MMC).
ΔP means the mean amplitude increase of the contractions of the pylorus (expressed in % MMC).
ΔD means the mean amplitude increase of the contractions of the duodenum (expressed in % MMC).

| Dose | Changes in amplitude (expressed in % MMC) | | | Improvement of |
|---|---|---|---|---|
| (mg/kg P.O.) | ΔA | ΔP | ΔD | coordination |
| 0.00031 | 5 | 21 | 9 | 3/4 |
| 0.00125 | 9 | 29 | 13 | 3/4 |
| 0.005 | 13 | 35 | 13 | 4/6 |
| 0.02 | 12 | 34 | 12 | 5/6 |
| 0.08 | 24 | 37 | 13 | 4/6 |
| 0.31 | 11 | 30 | 11 | 4/6 |

PHARMACOLOGICAL EXAMPLE P-2

Gastric emptying of an acaloric liquid test meal delayed by administration of lidamidine, in conscious dogs.

Female beagle dogs, weighing 7–14 kg, were trained to stand quietly in Pavlov frames. They were implanted with a gastric cannula under general anesthesia and aseptic precautions. After a median laparatomy, an incision was made through the gastric wall in the longitudinal direction between the greater and the lesser curve, 2 cm above the nerves of Latarjet. The cannula was secured to the gastric wall by means of a double purse string suture and brought out via a stab wound at the left quadrant of the hypochondrium. Dogs were allowed a recovery period of at least two weeks.

Experiments were started after a fasting period of 24 hours, during which water was available ad libitum. At the beginning of the experiment, the cannula was opened in order to remove any gastric juice or food remnants.

The stomach was cleansed with 40 to 50 ml lukewarm water. The test compound was administered I.V. (in a volume ≦3 ml via the vena cephalica), S.C. (in a volume ≦3 ml) or P.O. (in a volume of 1 ml/kg body weight, applied intragastrically via the cannula with a device that filled the lumen of the cannula; after injection of the test compound, 5 ml NaCl 0.9% was injected in order to correct for the dead space in the injection system). Immediately after administration of the test compound or its solvent, lidamidine 0.63 mg/kg was administered subcutaneously. 30 min later, the cannula was opened to determine the amount of fluid present in the stomach, promptly followed by reintroduction of the fluid. Then the test meal was administered via the cannula. This test meal consisted of 250 ml distilled water containing glucose (5 g/l) as a marker. The cannula remained closed for 30 min, whereafter the gastric contents were drained from the stomach to measure total volume (t=30 min). For later analysis 1 ml of the gastric contents was taken, promptly followed by reintroduction of the rest volume into the stomach. This sequence was repeated 4 times with 30 min intervals (t=60, 90, 120, 150 min).

In the 1 ml samples of the gastric contents, the glucose concentrations were measured on a Hitachi 717 automatic analyzer by the hexokinase method (Schmidt, 1961). These data were used to determine the absolute amount of glucose that remained in the stomach after each 30 min period, as a measure for the rest volume of the meal itself, independent of acid secretion.

Curves were fitted to the measurement points (glucose versus time) using weighed non-linear regression analysis. Gastric emptying was quantified as the time needed to empty 70% of the meal (t 70%). The control emptying time was calculated as the mean t 70% of the last 5 solvent experiments of the same dog. Acceleration of delayed gastric emptying (Δt) was calculated as the time difference between t 70% compound and t 70% solvent. To correct for variations in emptying rate between dogs, Δt was expressed as % of t 70% solvent (Schuurkes et al, 1992)).

TABLE P-2

Acceleration of gastric emptying of a liquid meal delayed by lidamidine in conscious dog by compound 30.

| Dose (mg/kg) | Acceleration expressed in ΔT/T |
|---|---|
| 0.00016 | +0.16 |
| 0.00063 | −0.26 |
| 0.0025 | −0.46 |
| 0.01 | −0.60 |
| 0.04 | −0.67 |

TABLE P-3

The acceleration of gastric emptying of a liquid meal delayed by lidamidine in conscious dog was measured for the following compounds at a dose of 0.0025 mg/kg.

| Co. No. | ΔT/T | | | | |
|---|---|---|---|---|---|
| 3 | −0.01 | 77 | −0.43 | 108 | −0.49 |
| 10 | −0.22 | 78 | −0.25 | 126 | −0.15 |
| 16 | −0.54 | 79 | −0.40 | 127 | −0.25 |
| 21 | −0.25 | 80 | −0.39 | 132 | −0.06 |
| 27 | −0.12 | 81 | −0.41 | 134 | −0.45 |
| 30 | −0.55 | 83 | −0.22 | 135 | −0.17 |
| 31 | −0.31 | 84 | −0.38 | 138 | −0.35 |
| 32 | −0.54 | 85 | −0.11 | 139 | −0.25 |
| 34 | −0.77 | 86 | −0.51 | 140 | −0.39 |
| 35 | −0.28 | 87 | −0.38 | 141 | −0.12 |
| 41 | −0.45 | 88 | −0.53 | 143 | −0.37 |
| 42 | −0.25 | 89 | −0.25 | 151 | −0.52 |
| 43 | −0.17 | 90 | −0.46 | 152 | −0.15 |
| 44 | −0.43 | 91 | −0.34 | 153 | −0.40 |
| 46 | −0.04 | 92 | −0.44 | 154 | −0.21 |
| 47 | −0.26 | 93 | −0.41 | 156 | −0.36 |
| 48 | −0.39 | 94 | −0.55 | 158 | −0.34 |
| 49 | −0.58 | 95 | −0.13 | 159 | −0.09 |
| 50 | −0.73 | 96 | −0.48 | 165 | −0.14 |
| 51 | −0.49 | 97 | −0.35 | 167 | −0.15 |
| 52 | −0.49 | 98 | −0.30 | 169 | −0.18 |
| 54 | −0.05 | 99 | −0.71 | 170 | −0.25 |
| 56 | −0.31 | 100 | −0.50 | 172 | −0.17 |
| 65 | −0.23 | 101 | −0.45 | 181 | −0.08 |
| 66 | −0.14 | 102 | −0.01 | 182 | −0.40 |
| 68 | −0.32 | 103 | −0.13 | 184 | −0.20 |
| 71 | −0.20 | 104 | −0.29 | 185 | −0.23 |
| 73 | −0.72 | 105 | −0.23 | | |
| 76 | −0.59 | 106 | −0.39 | | |
| | | 107 | 0.24 | | |

TABLE P-4

The acceleration of gastric emptying of a liquid meal delayed by lidamidine in conscious dog was measured for the following intermediates at a dose of 0.0025 mg/kg.

| Interm. No | ΔT/T |
|---|---|
| 6-j | −0.18 |
| 6-k | −0.49 |
| 6-l | −0.75 |
| 6-m | −0.30 |
| 7-a | −0.32 |

COMPOSITION EXAMPLES

The following formulations exemplify typical pharmaceutical compositions in dosage unit form suitable for systemic or topical administration to warm-blooded animals in accordance with the present invention.

"Active ingredient" (A.I.) as used throughout these examples relates to a compound of formula (I), a N-oxide form, a pharmaceutically acceptable acid or base addition salt or a stereochemically isomeric form thereof.

Example C-1

Oral Solutions 9 g of methyl 4-hydroxybenzoate and 1 g of propyl 4-hydroxybenzoate are dissolved in 4 l of boiling purified water. In 3 l of this solution are dissolved first 10 g of 2,3-dihydroxybutanedioic acid and thereafter 20 g of the A.I. The latter solution is combined with the remaining part of the former solution and 12 l of 1,2,3-propanetriol and 3 l of sorbitol 70% solution are added thereto. 40 g of sodium saccharin are dissolved in 0.5 l of water and 2 ml of raspberry and 2 ml of gooseberry essence are added. The latter solution is combined with the former, water is added q.s. to a volume of 20 l providing an oral solution comprising 5 mg of the A.I. per teaspoonful (5 ml). The resulting solution is filled in suitable containers.

Example C-2

Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the A.I.

Example C-3

Film-Coated Tablets
Preparpation of Tablet Core
A mixture of 100 g of the A.I., 570 g lactose and 200 g starch is mixed well and thereafter humidified with a solution of 5 g sodium dodecyl sulfate and 10 g polyvinylpyrrolidone in about 200 ml of water. The wet powder mixture is sieved, dried and sieved again. Then there are added 100 g microcrystalline cellulose and 15 g hydrogenated vegetable oil. The whole is mixed well and compressed into tablets, giving 10.000 tablets, each comprising 10 mg of the active ingredient.
Coating
To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinylpyrrolidone and 30 ml of concentrated color suspension and the whole is homogenated. The tablet cores are coated with the thus obtained mixture in a coating apparatus.

Example C-4

Injectable Solution 1.8 g methyl 4-hydroxybenzoate and 0.2 g propyl 4-hydroxybenzoate were dissolved in about 0.5 l of boiling water for injection. After cooling to about 50° C. there were added while stirring 4 g lactic acid, 0.05 g propylene glycol and 4 g of the A.I. The solution was cooled to room temperature and supplemented with water for injection q.s. ad 1 l volume, giving a solution of 4 mg/ml of A.I. The solution was sterilized by filtration and filled in sterile containers.

Example C-5

Suppositories

3 Grams A.I. was dissolved in a solution of 3 grams 2,3-dihydroxybutanedioic acid in 25 ml polyethylene glycol 400. 12 Grams surfactant and 300 grams triglycerides were molten together. The latter mixture was mixed well with the former solution. The thus obtained mixture was poured into molds at a temperature of 37–38° C. to form 100 suppositories each containing 30 mg/ml of the A.I.

What is claimed is:

1. A compound of formula (I)

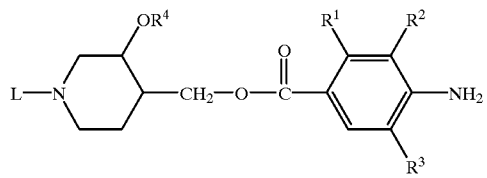

(I)

a stereochemically isomeric form thereof, an N-oxide form thereof or a pharmaceutically acceptable acid or base addition salt thereof, wherein $R^1$ is $C_{1-6}$alkyloxy, $C_{2-6}$alkenyloxy or $C_{2-6}$alkynyloxy;

$R^2$ is hydrogen or $C_{1-6}$alkyloxy, or taken together $R^1$ and $R^2$ may form a bivalent radical of formula —O—CH$_2$—O— (a-1), —O—CH$_2$—CH$_2$— (a-2), —O—CH$_2$—CH$_2$—O— (a-3), —O—CH$_2$—CH$_2$—CH$_2$— (a-4), —O—CH$_2$—CH$_2$—CH$_2$—O— (a-5), —O—CH$_2$—CH$_2$—CH$_2$—CH$_2$— (a-6), wherein in said bivalent radicals one or two hydrogen atoms may be substituted with $C_{1-6}$alkyl, $R^3$ is hydrogen or halo;

$R^4$ is hydrogen or $C_{1-6}$alkyl;

L is $C_{3-6}$cycloalkyl, $C_{5-6}$cycloalkanone, $C_{2-6}$alkenyl optionally substituted with aryl, or L is a radical of formula —Alk—$R^5$ (b-1), —Alk—X—$R^6$ (b-2), —Alk—Y—C(=O)—$R^8$ (b-3), or —Alk—Y—C(=O)—NR$^{10}$R$^{11}$ (b-4), wherein each Alk is $C_{1-12}$alkanediyl; and $R^5$ is hydrogen, cyano, $C_{1-6}$alkylsulfonylamino, $C_{3-6}$cycloalkyl, $C_{5-6}$cycloalkanone, aryl, di(aryl)methyl or Het$^1$;

$R^6$ is hydrogen, $C_{1-6}$alkyl, hydroxy$C_{1-6}$alkyl, $C_{3-6}$cycloalkyl, aryl or Het$^2$;

X is O, S, SO$_2$ or NR$^7$; said $R^7$ being hydrogen, $C_{1-6}$alkyl or aryl;

$R^8$ is hydrogen, $C_{1-6}$alkyl, $C_{3-6}$cycloalkyl, aryl, arylC$_{1-6}$alkyl, di(aryl)methyl, $C_{1-6}$alkyloxy or hydroxy;

Y is NR$^9$ or a direct bond; said $R^9$ being hydrogen, $C_{1-6}$alkyl or aryl;

$R^{10}$ and $R^{11}$ each independently are hydrogen, $C_{1-6}$alkyl, $C_{3-6}$cycloalkyl, aryl or arylC$_{1-6}$alkyl, or $R^{10}$ and $R^{11}$ combined with the nitrogen atom bearing $R^{10}$ and $R^{11}$ may form a pyrrolidinyl or piperidinyl ring both being optionally substituted with $C_{1-6}$alkyl, amino or mono or di($C_{1-6}$alkyl)amino, or said $R^{10}$ and $R^{11}$ combined with the nitrogen bearing $R^{10}$ and $R^{11}$ may form a piperazinyl or 4-morpholinyl radical both being optionally substituted with $C_{1-6}$alkyl;

each aryl being unsubstituted phenyl or phenyl substituted with 1, 2 or 3 substituents each independently selected from halo, hydroxy, $C_{1-6}$alkyl, $C_{1-6}$alkyloxy, aminosulfonyl, $C_{1-6}$alkylcarbonyl, nitro, trifluoromethyl, amino or aminocarbonyl; and Het$^1$ and Het$^2$ each independently are selected from furanyl; furanyl substituted with $C_{1-6}$alkyl or halo; tetrahydrofuranyl; a tetrahydrofuranyl substituted with $C_{1-6}$alkyl; a dioxolanyl; a dioxolanyl substituted with $C_{1-6}$alkyl, a dioxane; a dioxane substituted with $C_{1-6}$alkyl; tetrahydropyranyl; a tetrahydropyranyl substituted with $C_{1-6}$alkyl; pyrrolidinyl; pyrrolidinyl substituted with one or two substituents each independently selected from halo, hydroxy, cyano, or $C_{1-6}$alkyl; pyridinyl; pyridinyl substituted with one or two substituents each independently selected from halo, hydroxy, cyano, $C_{1-6}$alkyl; pyrimidinyl; pyrimidinyl substituted with one or two substituents each independently selected from halo, hydroxy, cyano, $C_{1-6}$alkyl, $C_{1-6}$alkyloxy, amino and mono and di($C_{1-6}$alkyl)amino; pyridazinyl; pyridazinyl substituted with one or two substituents each independently selected from hydroxy, $C_{1-6}$alkyloxy, $C_{1-6}$alkyl or halo; pyrazinyl; pyrazinyl substituted with one ore two substituents each independently selected from halo, hydroxy, cyano, $C_{1-6}$alkyl, $C_{1-6}$alkyloxy, amino, mono- and di($C_{1-6}$alkyl)amino and $C_{1-6}$alkyloxycarbonyl;

Het$^1$ can also be a radical of formula

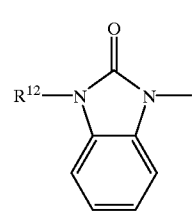

(c-1)

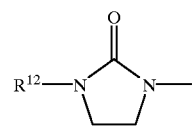

(c-2)

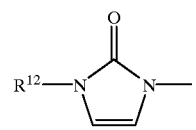

(c-3)

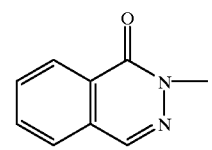

(c-4)

Het$^1$ and Het$^2$ each independently can also be selected from the radicals of formula

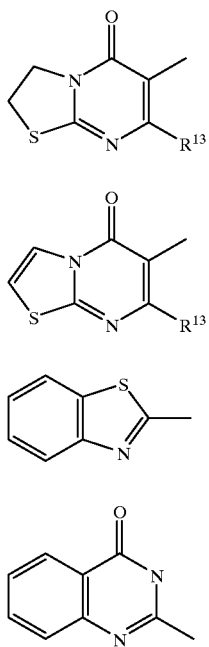

$R^{12}$ and $R^{13}$ each independently are hydrogen or $C_{1-4}$alkyl.

2. A compound as claimed in claim 1 wherein $R^1$ is methoxy, $R^2$ is hydrogen; or wherein $R^1$ and $R^2$ are taken together to form a radical of formula (a-2), (a-3) or (a-4); and $R^3$ is chloro.

3. A compound according to claim 2 wherein the hydroxy or methoxy is in the trans position in relation to the methylene on the central piperidine moiety.

4. A compound according to the claim 3 wherein the compound is (±)-trans-(1-butyl-3-hydroxy-4-piperidinyl)methyl 8-amino-7-chloro-2,3-dihydro-1,4-benzodioxin-5-carboxylate, a pharmaceutically acceptable acid addition salt thereof or a stereochemically isomeric form thereof.

5. A pharmaceutical composition comprising a pharmaceutically acceptable carrier and a therapeutically active amount of a compound as claimed in claim 1.

6. A method of treating a condition related to a hampered or impaired gastric emptying comprising administering to a warm-blooded animal in need thereof an effective amount of a compound of claim 1.

7. A method of claim 6, wherein the condition is gastrooesophageal reflux, dyspepsia, gastroparesis, constipation, post-operative ileus or intestinal pseudo-obstruction.

8. A process for preparing a compound of formula I as claimed in claim 1 comprising reacting an intermediate of formula (II)

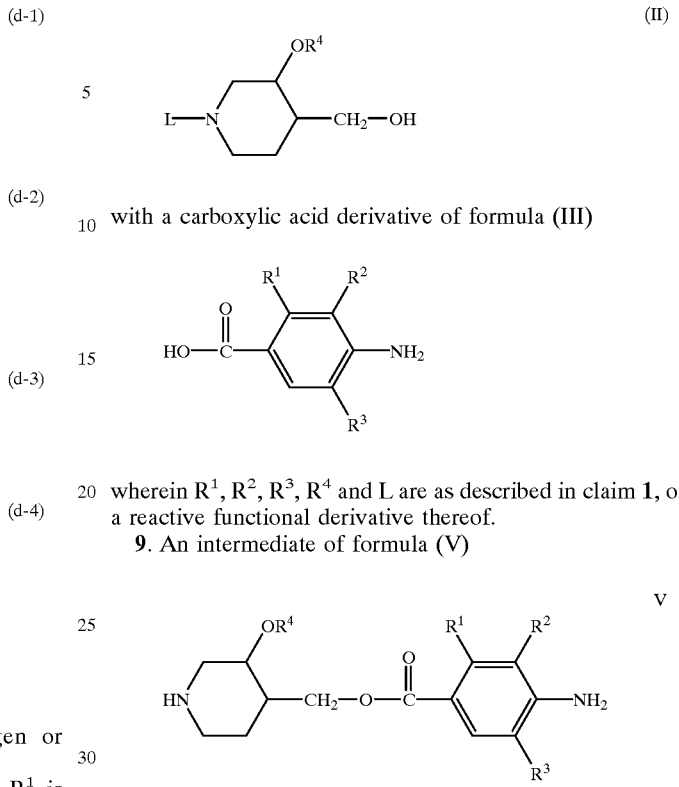

with a carboxylic acid derivative of formula (III)

wherein $R^1$, $R^2$, $R^3$, $R^4$ and L are as described in claim 1, or a reactive functional derivative thereof.

9. An intermediate of formula (V)

a pharmaceutically acceptable acid addition salt thereof or a stereochemically isomeric form thereof, wherein $R^1$ is $C_{1-6}$alkyloxy, $C_{2-6}$alkenyloxy or $C_{2-6}$alkynyloxy;

$R^2$ is hydrogen or $C_{1-6}$alkyloxy, or taken together $R^1$ and $R^2$ may form a bivalent radical of formula

| | |
|---|---|
| —O—CH$_2$—O— | (a-1), |
| —O—CH$_2$—CH$_2$— | (a-2), |
| —O—CH$_2$—CH$_2$—O— | (a-3), |
| —O—CH$_2$—CH$_2$—CH$_2$— | (a-4), |
| —O—CH$_2$—CH$_2$—CH$_2$—O— | (a-5), |
| —O—CH$_2$—CH$_2$—CH$_2$—CH$_2$— | (a-6), | wherein in said bivalent radicals one or two hydrogen atoms may be substituted with $C_{1-6}$alkyl, $R^3$ is hydrogen or halo; and $R^4$ is hydrogen or $C_{1-6}$alkyl.

* * * * *

UNITED STATES PATENT AND TRADEMARK OFFICE
CERTIFICATE OF CORRECTION

PATENT NO.   : 6,096,761
DATED        : August 1, 2000
INVENTOR(S)  : Jean-Paul Rene Marie Bosmans et al.

Page 1 of 1

It is certified that error appears in the above-identified patent and that said Letters Patent is hereby corrected as shown below:

Title page,
Item [22], PCT Filed: please delete "February 11, 1997" and insert therefore
-- February 7, 1997 --

Signed and Sealed this

Thirty-first Day of August, 2004

JON W. DUDAS
*Director of the United States Patent and Trademark Office*